US008501913B2

(12) United States Patent
Grbic et al.

(10) Patent No.: US 8,501,913 B2
(45) Date of Patent: Aug. 6, 2013

(54) SPIDER MITE SILK PROTEINS

(75) Inventors: Miodrag Grbic, Ontario (CA); Vojislava Grbic, Ontario (CA); Stephane Rombauts, Ghent (BE); Yves Van De Peer, Ghent (BE)

(73) Assignees: VIB VZW, Ghent (BE); Universiteit Gent, Ghent (BE); The University of Western Ontario, London, Ontario (CA)

( * ) Notice: Subject to any disclaimer, the term of this patent is extended or adjusted under 35 U.S.C. 154(b) by 0 days.

(21) Appl. No.: 13/499,890

(22) PCT Filed: Oct. 1, 2010

(86) PCT No.: PCT/EP2010/064632
§ 371 (c)(1),
(2), (4) Date: Jun. 7, 2012

(87) PCT Pub. No.: WO2011/039345
PCT Pub. Date: Apr. 7, 2011

(65) Prior Publication Data
US 2012/0245326 A1 Sep. 27, 2012

(30) Foreign Application Priority Data
Oct. 2, 2009 (EP) .................................... 09172104

(51) Int. Cl.
*A61K 38/17* (2006.01)
*C12P 21/06* (2006.01)
*C12P 21/04* (2006.01)

(52) U.S. Cl.
USPC .......................... 530/353; 435/69.1; 435/71.1

(58) Field of Classification Search
None
See application file for complete search history.

(56) References Cited

FOREIGN PATENT DOCUMENTS

| WO | WO 91/16351 | 10/1991 |
|----|-------------|---------|
| WO | WO 99/47661 | 9/1999 |
| WO | WO 01/05333 | 7/2001 |
| WO | WO 2011/039345 | 4/2011 |

OTHER PUBLICATIONS

Craig et al., A comparison of the composition of slk proteins produced by spiders and insects; International Journal of Biological Macromolecules 24 (1999) 109-118.
Grbic et al.. Mity model: *Tetranychus urticae*, a candidate for chelicerate model organism; BioEssays29:489-496; 2007.
Collin et al.; Characterization of silk spun by the embiopteran, *Antipaluria urichi*; Insect Biochemistry and Molecular Biology; 39 (2009) 75-82.
Collin et al.; Characterization of silk spun by the embiopteran, *Antipaluria urichi*; XP002619960; Dec. 16, 2008.
Craig et al., A comparison of the composition of silk proteins produced by spiders and insects; International Journal of Biological Macromolecules 24 (1999) 109-118.
Grbic et al..; Mity model: *Tetranychus urticae*, a candidate for chelicerate model organism; BioEssays29:489-496; 2007.
Hazan et al.; Spider Mite Webbing—III. Solubilization and Amino Acid Composition of the Silk Protein; Comp. Biochem. Physiol., 1975, vol. 51B, pp. 457-462.
International Search Report; PCT/EP2010/064632 dated Feb. 23, 2011.
Teule et al.; A protocol for the production of recombinant spider silklike proteins for artificial fiber spinning; Nature Protocols; vol. 4, No. 3; 2009; pp. 341-355.
Tian et al.; Analysis of Major Ampullate Silk cDNAs from Two NonOrb-Weaving Spiders; Bio Macromolecules; vol. 5, No. 3; May/Jun. 2004; pp. 657-660.
Tian et al.; Analysis of Major Amullate Silk cDNAs from Two NonOrb-Weaving Spiders; XP-002619958; Jul. 5, 2004.

*Primary Examiner* — Manjunath Rao
*Assistant Examiner* — Gerard Lacourciere
(74) *Attorney, Agent, or Firm* — TraskBritt

(57) ABSTRACT

Described are silk proteins derived from spider mite, more specifically derived from *Tetranychus urticae*. More specifically, described is the use of these proteins to make fibers, or fiber-composed material and the resulting fibers and materials.

15 Claims, No Drawings

SPIDER MITE SILK PROTEINS

CROSS-REFERENCE TO RELATED APPLICATION(S)

This is a national phase entry under 35 U.S.C. §371 of International Patent Application PCT/EP2010/064632, filed Oct. 1, 2010, published in English as International Patent Publication WO 2011/039345 A1 on Apr. 7, 2011, which claims benefit under Article 8 of the Patent Cooperation Treaty to European Patent Application Serial No. 09172104.3, filed Oct. 2, 2009.

STATEMENT ACCORDING TO 37 C.F.R. §1.821(c) or (e)—SEQUENCE LISTING SUBMITTED AS ASCII TEXT FILE

Pursuant to 37 C.F.R. §1.821(c) or (e), a file containing an ASCII text version of the Sequence Listing has been submitted concomitant with this application, the contents of which are hereby incorporated by reference.

TECHNICAL FIELD

The disclosure relates to silk proteins derived from spider mite, more specifically derived from *Tetranychus urticae*. More specifically, the disclosure relates to the use of these proteins to make fibers or fiber-composed material.

BACKGROUND

Silk is a secreted, fibrous material that is deposited or spun by an organism. From a biochemical point of view, silk consists of protein threads composed of repeating arrays of polypeptides that contain both discrete crystalline and non-crystalline domains that are oriented around a fiber axis.

Several arthropods, such as spiders, caterpillars mites, mantids, moths, and beetles, produce silk, or silk-like fibers. Insects, as a group, as well as spiders, produce many different types of silks and fibrous proteins, such as fibroins and spidroins. An individual spider may produce as many as nine different types of silks and fibrous proteins, each of which may be composed of more than one type of protein (Kovoor 1987; Haupt & Kovoor 1993). Different silks differ in number as well as in sequence of composing proteins. Although all fibroin and spidroin proteins do comprise several repeats, the repeat structures are species dependent and the amino acid composition, as well as the mechanical characteristics, may vary strongly from silk to silk (Zurovec and Sehnal 2002; Fedic et al. 2003).

Although the domesticated silkworm *Bombyx mori* is the mainstay of the silk industry, there is a considerable trade in some countries in silk produced by silkworms living "wild." The most important of these wild silks are those that are known as Tussah. Tussah is the product of several species of silkworm of the genus *Antheraea*, particularly *Antheraea mylitta*, indigenous to India, and *Antheraea pernyi*, which is native to China (Huber 1947; Cook 1984). Although Tussah silk is the most important wild silk in commercial use, there are still other varieties of caterpillars that produce silk. These silks are called wild, because these worms are not capable of being domesticated and artificially cultivated. Some examples are: *Antheraea yamamai, Attacus ricini*, and *Attacus Atlas*.

In recent years, spider silk was receiving more and more interest, mainly due to the excellent mechanical characteristics of this silk. For spiders, one species can make different silk fibers for different purposes, such as dragline silk or major ampullate silk, capture-spiral silk, tubuliform silk, aciniform silk and minor-ampullate silk.

The most investigated type of spider silk is the dragline or major ampullate (MA) silk that is secreted by the major ampullate glands of the spider. The dragline is used to support the spider when constructing a web and to prevent it from falling. This function results in mechanical properties combining a high Young's modulus with a high strength. Due to its size and accessibility, the major ampullate gland has been the focus of most studies.

A second important type of spider silk is the flagelliform, spiral or capture silk. This type of silk is composed of an acidific glycoprotein, secreted from the flagelliform gland, and coated with glue from the aggregate gland, which makes it sticky. The glue is not regarded as silk because it is composed of glycoproteins and other amino acids. The flagelliform silk is exclusively used for the construction of the spiral components of the web. This function results in a fiber that is highly extensible and capable of absorbing the energy of the flying prey without failure. The functional role of the glue is believed to allow for more effective capture of prey.

Minor ampullate (MI) silk is the spider silk that is secreted by the minor ampullate glands and is a strong, non-elastic, deformably stretchable silk used in web formation (Colgin & Lewis 1998).

Another spider silk that is discussed in this text is the egg sac silk that is used to wrap eggs. Vollrath (1992, 2000) mentioned in his representation of the spinning glands associated to its function that the soft inner silk of the egg sac is produced by the aciniform glands (aciniform silk), whereas the tough outer silk of the egg sac is secreted by the cylindrical or tubuliform spinning glands (tubuliform silk). Viney et al. (2000) believes the opposite. The tubuliform glands are only found in female spiders, which makes it more probable that the inner silk is indeed secreted by the tubuliform glands.

Because of its attractive properties (high strength, flexible with good water-absorbing power, soft, good elastic recovery behavior, glossiness, etc.), silk has a wide variety of uses in the apparel, drapery, upholstery and military fields. Natural silk has a long history of use as a textile fiber, and has been used in recent years for medical sutures, blood vessels, artificial skin, tendons and for binding enzymes (Bunning et al. 1994; Kuzuhara et al. 1987). Interest in *Antheraea pernyi* silk for biomedical applications has recently grown because *A. pernyi* SF contains the tripeptide sequence of arg-gly-asp (RGD), known as cell adhesive site for mammalian cell culture (Minoura et al. 1995; Pierschbacher & Ruoslahti 1984a, 1984b; Li et al. 2003). Therefore, it has been investigated as a potential biomaterial such as a matrix for the enzyme immobilization and mammalian fibroblast cell culture (Kweon et al. 2001a, 2001b). Silk of the spider *Nephila clavipes* has been used to help mammalian neural regeneration (Allmeling et al. 2006).

As each silk has its own composition and characteristics, there is a lot of interest in the identification of new silk proteins, opening the possibility for new applications. Surprisingly, we found that spider mites, and particularly *Tetranychus urticae*, are making silk proteins of which the amino acid composition differs rather strongly from that of classical fibroins and spidroins, especially in the alanine, glycine and serine content. Those differences are found in the global protein composition, as well as in the composition of the repeats.

DISCLOSURE

A first aspect of the disclosure is a spider mite silk protein, comprising a sequence selected from the group consisting of SEQ ID NO:1 through SEQ ID NO:19, or a homologue thereof. "Homologues," as used herein, means protein with at least 70%, preferably at least 80%, even more preferably at least 90% identities, as measured using BLASTp (Altschul et al. 1997). Preferably, the spider mite is *Tetranychus urticae*. Preferably, the proteins have a composition comprising at least 40%, preferably at least 45%, even more preferably at least 50% serine and glycine (taking both amino acids together), whereby the individual composition of serine and glycine for each is at least 15%, preferably at least 18%, even more preferably at least 20%, calculated as percentage of the number of the specific amino acid on the total number of amino acids. Even more preferably, independent of the percentage of glycine, serine is present in at least 21%, preferably at least 26%, even more preferably at least 30%. Even more preferably, the proteins comprise, beside the serine and glycine content, also at least 15%, preferably at least 17%, even more preferably at least 20% of alanine. One preferred embodiment is a spider mite silk protein, whereby the protein is selected from the group consisting of SEQ ID NO:1, SEQ ID NO:3, SEQ ID NO:4, SEQ ID NO:8, SEQ ID NO:9, SEQ ID NO:11, SEQ ID NO:12, SEQ ID NO:13, SEQ ID NO:14, SEQ ID NO:15, SEQ ID NO:16, and SEQ ID NO:17. An even more preferred embodiment is a spider mite silk protein whereby the protein is selected from the group consisting of SEQ ID NO:8, SEQ ID NO:13 and SEQ ID NO:15. The most preferred embodiment is a spider mite silk protein selected from the group consisting of SEQ ID NO:3, SEQ ID NO:9, SEQ ID NO:12, SEQ ID NO:14, and SEQ ID NO:17.

Another aspect hereof is a nucleic acid molecule encoding a protein according to the invention, or the complement thereof, or a functional fragment thereof. "Nucleic acid molecule," as used herein, refers to a polymeric form of nucleotides of any length, either ribonucleotides or deoxyribonucleotides. This term refers only to the primary structure of the molecule. Thus, this term includes double- and single-stranded DNA, and RNA under the forms known to the person skilled in the art, such as, but not limited to, genomic DNA, cDNA, mRNA, antisense RNA and RNAi. It also includes known types of modifications, for example, methylation, "caps" substitution of one or more of the naturally occurring nucleotides with an analog. One preferred embodiment of a functional fragment is a fragment that can be used as RNAi.

Still another aspect hereof is a recombinant host cell, comprising a nucleic acid molecule according to the invention. A "recombinant host cell," as used here, is a cell that has been genetically modified, preferably by the introduction of a nucleic acid according to the invention. The recombinant host cell of the invention can be any prokaryotic or eukaryotic cell, including, but not limited to, bacterial cells such as *Escherichia coli*, yeast cells, such as *Saccharomyces spp*, *Pichia* spp, or *Kluyveromyces* spp, insect cells, plant cells or mammalian cells. The recombinant host cells can be used to produce large quantities of the spider mite silk protein according to the invention. Methods for the production of recombinant silk proteins are known to the person skilled in the art and have been described, as a non-limiting example, in WO9116351 and WO9947661, hereby incorporated herein by this reference.

Another aspect of the invention is the use of a spider mite silk protein, according to the invention, to make a fiber. Methods to make artificial silk fibers using silk proteins are known to the person skilled in the art and have been disclosed, as a non-limited example, in WO0153333 and in Teulé et al. (2009), hereby incorporated herein by this reference.

Still another aspect of the invention is an artificially produced fiber, comprising one or more proteins of the invention. "Artificially produced," as used here, means that the fiber and/or the composing proteins are not produced by a naturally occurring *Tetranychus urticae*.

DETAILED DESCRIPTION OF THE INVENTION

EXAMPLES

Example 1

Sequencing of the *Tetranychus urticae* Genome

The London population of *T. urticae* developed from the isofemale line in London Ontario, following eight backcrosses (to generate maximum homozygote population) was mass produced on the bean plants in growth chambers at 27° C. and 16:8 photoperiod. Plants were washed in 0.1% TRITON X detergent solution in 2-liter beakers to release all spider mite life stages. Adult spider mites, nymphs, larvae and eggs were filtered through series of fine sieves to isolate pure egg fraction. Eggs were collected in the Eppendorf tube, treated with bleach solution (to remove plant tissue and possible microbial contaminants) and prepared for the DNA extraction. Embryos were ground in the glass tissue grinder and DNA extraction was performed using QUIAGEN Blood&cell culture DNA kit (Midi column #13433) according to manufacturer's protocol. DNA for whole genome sequencing project was sequenced using Sanger sequencing protocol at the Joint Genome Institute (USA Department of Energy), Walnut Creek, Calif.

Example 2

Identification of the Genes

From fragments of fibroin genes available in the database, blastp and tblastn were run over the proteome and genome of *Tetranychus urticae*. The obtained hits were all checked manually as due to the highly repeated nature of the sequence problems occurred with the prediction and even assembly of the original genomic sequence. About half of the gene models were originally wrongly predicted, involving incorrectly predicted reading frames. The corrections were iteratively evaluated and aligned using MUSCLE, including the existing fibroin genes from the public databases and the already found (and corrected) genes found in *Tetranychus urticae*.

The originally found proteins all had in common a high percentage of G, A and P organized in repetitive patterns. This particular aspect was further used to identify more divergent proteins having similar patterns. To find them, tblastn was run again with the low-complexity filters turned off. From the multiple hits returned, six more genes were retained, based on similarity of patterns and coverage by Illumina transcript reads. All were manually annotated and added to the already found genes, as potentially involved in the fibers. In total, twelve genes were found having a similar repetitive domain.

Example 3

Analysis of the Spider Mite Silk

Mechanical and antimicrobial characteristics of the spider mite silk are investigated. Thread thickness and strength are measured using the standard techniques.

The FAVIMAT-ROBOT (Textechno) is used to analyze the tensile properties. It is a semi-automatic single-strength tester, working according to the principle of constant rate of extension (DIN 51221, DIN 53816, ISO 5079). The instrument is equipped with a balance allowing the mass to be measured at a high resolution of 0.1 mg. The instrument includes a ROBOT, which is a fiber storage, equipped with a computer-controlled transfer clamp for the transport of the single fiber to the testing position of the FAVIMAT. Moreover, this instrument is equipped with an integrated measuring unit for linear density (in dtex=0.1 g/km). This has the considerable advantage, certainly for natural fibers, that the fineness is determined simultaneously with the tensile properties. The linear density is measured according to the vibroscopic method (ASTM D 1577—BISFA 1985/1989 chapter F). The fiber is preloaded at a predefined speed. Further on, the fiber is subjected to an electro-acoustic sinusoidal vibration and the resonance frequency is detected with an opto-electronic sensor. The fiber linear density is calculated from the resonance condition, i.e., length, preload, and resonance frequency of the fiber. Suggesting a uniform mass distribution and a round cross-section, the linear density can be calculated as follows:

$$T_t = \frac{F_v \cdot 10^{11}}{4 \cdot f^2 \cdot L^2}$$

In this equation, Tt is the linear density in dtex, Fv is the preload in cN, f is the resonance frequency and L is the test length in mm.

As spider mite silk is very resistant to degradation, possible antimicrobial activity of the silk is measured by measuring the inhibition circle around the silk on solid medium Example 4

Confirmation of the Presence of the Proteins in Spider Mite Silk by Mass Spectrometry (MS) Analysis Ten *T. urticae* adults were placed into capped and Parafilm-sealed 35 mm Petri plates for 24 hours at room temperature. Petri plate cap was removed and examined for signs of mites, eggs and debris, which were removed as necessary. After this, a cap was washed with 1 mL of 95% ethanol and silk threads suspended in ethanol were collected in Eppendorf tubes. Content of 10-15 tubes was pooled together and silk threads were transferred to a glass container for a wash with acetic acid. Silk threads were transferred back into 95% ethanol, pulled apart, and transferred into Eppendorf tubes with 95% ethanol for storage and subsequent analysis. Silk thread suspensions were initially evaporated using a SpeedVac system. The dried samples were re-suspended in 75% TFA (trifluoroacetic acid) in glass vials. Vials were then microwaved for 45 minutes at full power in a beaker filled with water. The contents of the vials were then dried using a SpeedVac system and, following this, reconstituted in 10% formic acid. Samples were then injected on a Q-ToF MS system using a 150 minute 0-40% ACN gradient acquiring data in a data-dependent fashion. Data analysis was performed using Peaks Studio 5.2 software. Peptides were matched against *T. urticae* proteome database. Analysis was performed both with and without consideration for possible variable post-translational modifications, such as deamidation and oxidation.

Protein ID matches from *T. urticae* proteome database that appeared in both types of analysis and were also predicted using computational approach were considered for subsequent amplification and cloning by means of PCR. SEQ ID NO:3, SEQ ID NO:14, and SEQ ID NO:17 have been confirmed as being part of the silk by MS.

Example 5

Use of the Polymerase Chain Reaction (PCR) to Confirm Gene Expression

*T. urticae* RNA was extracted using Trizol reagent (Invitrogen). Samples for PCR were prepared by reverse transcribing 3 µg of total RNA using Superscript II Reverse Transcriptase (Invitrogen). Aliquots of this reaction were then used in PCR reactions. Primers for PCR were designed to amplify short (100-200 bp) fragments from the non-repetitive 5' and 3' regions of candidate genes predicted mRNA sequence. PCR was performed using Taq DNA Polymerase (Fermentas) according to manufacturer's recommendations and amplified fragments were cloned into pGEM-T Easy vector (Promega) for sequencing. SEQ ID NO:9, SEQ ID NO:12 and SEQ ID NO:17 were confirmed as being expressed as mRNA by PCR.

References

Allmeling C., A. Jokuszies, K. Reimers, S. Kall, and P. M. Vogt (2006). Use of spider silk fibers as an innovative material in a biocompatible nerve conduit. *J. Cell. Mol. Med.* 10:770-777.

Altschul S. F., T. L. Madden, A. A. Schäffer, J. Zhang, Z. Zhang, W. Miller, and D. J. Lipman (1997). Gapped BLAST and PSI-BLAST: a new generation of protein database search programs. *Nucl. Acids. Res.* 25:3389-3402.

Bunning T. J., H. Jiang, W. W. Adams, R. L. Crane, B. Farmer, and D. Kaplan (1994). In: *Silk Polymers—Materials Science and Biotechnology*, D. Kaplan, W. W. Adams, B. Farmer, and C. Viney (Eds.), American Chemical Society, Washington D.C., ACS Symposium Series, 544:353-358.

Colgin M. A. and R. V. Lewis (1998). Spider minor ampullate silk proteins contain new repetitive sequences and highly conserved non-silk-like "spacer regions." *Protein Science* 7:667-672.

Cook J. G. (1984). Handbook of Textile Fibres—Natural Fibres, Merrow Publishing Co. Ltd., Durham, England, 144-165.

Haupt J. and J. Kovoor (1993). Silk-gland system and silk production in *Mesothelae (Araneae)*. Annales des Sciences Naturelles, *Zoology*, Paris 14:35-48.

Huber C. J. (1947). The silk fibers in *Matthew's textile fibers—Their physical, microscopical and chemical properties*, H. R. Mauersberger (Ed.), 5th edition, John Wiley & Sons Inc., New York, Chapter XVII, 679-729.

Fedic R., M. Zurovec, and F. Sehnal (2003). Correlation between fibroin amino acid sequence and physical silk properties. *J. Biol. Chem.* 278:35255-35264.

Kovoor J. (1987). Comparative structure and histochemistry of silk-producing organs in arachnids. In: *The Ecophysiology of Spiders*, W. Nentwig and S. Heimer S. (Eds.), Springer-Verlag, New York, 160-186.

Kuzuhara A., T. Asakura, R. Tomoda and T. Matsunaga T. (1987). Use of silk fibroin for enzymemembrane. *J. Biotechnol.* 5:199-207.

Kweon H. Y., I. C. Um and Y. H. Park (2001a). Structural and thermal characteristics of *Antheraea pernyi* silk fibroin/chitosan blend film. *Polymer* 42:6651-6656.

Kweon H., S. O. Woo and Y. H. Park (2001b). Effect of heat treatment on the structural and conformational changes of regenerated *Antheraea pernyi* silk fibroin films. *J. Appl. Polym. Sci.* 81:2271-2276.

Li M. Z., W. Tao, S. Kuga and Y. Nishiyama (2003). Controlling molecular conformation of regenerated wild silk fibroin by aqueous ethanol treatment. *Polymers for Advanced Technologies* 14:694-698.

Minoura N., S. Aiba, Y. Gotoh, M. Tsukada and Y. Imai (1995). Attachment and growth of fibroblast cells on silk fibroin. *Biochem. Biophys. Res. Commun.* 208:511-516.

Pierschbacher M. D. and E. Ruoslahti (1984a). Cell attachment activity of fibronectin can be duplicated by small synthetic fragments of the molecule? *Nature* 309:30-33.

Pierschbacher M. D. and E. Ruoslahti (1984b). Variants of the cell recognition site of fibronectin that retain attachment-promoting activity. *Proc. Natl. Acad. Sci. USA* 81:5985-5988.

Teulé F., A. R. Cooper, W. A. Furin, D. Bittencourt, E. L. Rech, A. Brooks, and R. V. Lewis (2009). A protocol for the production of recombinant spider silk-like proteins for artificial spinning *Nat. Protoc.* 4:341-345.

Viney C. (2000). From natural silks to new polymer fibers. *J. Text. Inst.* 91:2-23 Part 3 Sp. Iss. SI.

Vollrath F. (1992). Spider Webs and Silks. *Scientific American* 266:52-58.

Vollrath F. (2000). Strength and function of spiders' silks. *Reviews in Molecular Biotechnology* 74:67-83.

Zurovec M. and F. Sehnal (2002). Unique molecular architecture of silk fibroin in the waxmoth, *Galleria mellonella*. *J. Biol. Chem.* 277:22639-22647.

---

What is claimed is:

1. An isolated spider mite silk protein comprising a peptide selected from the group consisting of SEQ ID NO:8, SEQ ID NO:13, a peptide sequence having at least 90% identity to SEQ ID NO:8 and a peptide sequence having at least 90% identity to SEQ ID NO:13.

2. A spider mite silk protein of claim 1 comprising at least 40% serine and glycine wherein the individual content of serine and glycine for each is at least 15%.

3. The spider mite silk protein of claim 2, wherein the content of serine is at least 21%.

4. The spider mite silk protein of claim 1, wherein the spider mite is *Tetranychus urticae*.

5. The spider mite silk protein of claim 2, wherein the spider mite is *Tetranychus urticae*.

6. The spider mite silk protein of claim 3, wherein the spider mite is Tetranychus urticae.

7. A method of producing a spider mite silk protein, the method comprising expressing an isolated nucleic acid molecule encoding the spider mite silk protein of claim 1.

8. A method of producing a spider mite silk protein, the method comprising expressing an isolated nucleic acid molecule encoding the spider mite silk protein of claim 2.

9. A method of producing a spider mite silk protein, the method comprising expressing an isolated nucleic acid molecule encoding the spider mite silk protein of claim 3.

10. A method of producing a spider mite silk protein, the method comprising expressing an isolated nucleic acid molecule encoding the spider mite silk protein of claim 4.

11. A method of producing a spider mite silk protein, the method comprising:

transforming an isolated host cell with an isolated nucleic acid molecule encoding the spider mite silk protein of claim 1 to produce a recombinant host cell, comprising the nucleic acid molecule of claim 15 and expressing the isolated nucleic acid molecule in the recombinant host cell.

12. A fiber comprising the spider mite silk protein of claim 6.

13. A fiber comprising the spider mite silk protein of claim 5.

14. An artificially produced fiber comprising a spider mite silk protein selected from the group consisting of:

a) spider mite silk protein comprising a peptide-selected from the group consisting of SEQ ID NO:8 SEQ ID NO:13 a peptide sequence having at least 90% identity to SEQ ID NO:8 and a peptide sequence having at least 90% identity to SEQ ID NO:13.

b) spider mite silk protein of part a) comprising at least 40% serine and glycine wherein the individual content of serine and glycine for each is at least 15%; and c) spider mite silk protein of part a) comprising at least 40% serine and glycine wherein the individual content of glycine is at least 15%, and the content of serine is at least 21%.

15. A recombinantly produced protein comprising a peptide having the amino acid sequence selected from the group consisting of SEQ ID NO:8 SEQ ID NO:13 a peptide sequence having at least 90% identity to SEQ ID NO:8 and a peptide sequence having at least 90% identity to SEQ ID NO:13.

* * * * *

UNITED STATES PATENT AND TRADEMARK OFFICE
CERTIFICATE OF CORRECTION

PATENT NO. : 8,501,913 B2  
APPLICATION NO. : 13/499890  
DATED : August 6, 2013  
INVENTOR(S) : Miodrag Grbic et al.

Page 1 of 1

It is certified that error appears in the above-identified patent and that said Letters Patent is hereby corrected as shown below:

In the claims:

| | | | |
|---|---|---|---|
| CLAIM 2, | COLUMN 77, | LINE 63, | change "A spider" to --The spider-- |
| CLAIM 6, | COLUMN 78, | LINE 63, | change "Tetranychus urticae." to --*Tetranychus urticae.*-- |
| CLAIM 7, | COLUMN 78, | LINE 64, | change "a spider" to --the spider-- |
| CLAIM 8, | COLUMN 79, | LINE 1, | change "a spider" to --the spider-- |
| CLAIM 9, | COLUMN 79, | LINE 4, | change "a spider" to --the spider-- |
| CLAIM 10, | COLUMN 79, | LINE 7, | change "a spider" to --the spider-- |
| CLAIM 11, | COLUMN 79, | LINES 14-15, | change "cell, comprising the nucleic acid molecule of claim 15 and expressing" to --cell, and expressing-- |
| CLAIM 14, | COLUMN 80, | LINE 3, | change "a) spider" to --a) a spider-- |
| CLAIM 14, | COLUMN 80, | LINE 8, | change "b) spider" to --b) a spider-- |
| CLAIM 14, | COLUMN 80, | LINE 11, | change "c) spider" to --c) a spider-- |
| CLAIM 15, | COLUMN 80, | LINE 17, | change "NO:8 SEQ ID NO:13" to --NO:8, SEQ ID NO:13,-- |

Signed and Sealed this  
Fifteenth Day of September, 2015

Michelle K. Lee  
*Director of the United States Patent and Trademark Office*

SEQUENCE LISTING

```
<160> NUMBER OF SEQ ID NOS: 19

<210> SEQ ID NO 1
<211> LENGTH: 1172
<212> TYPE: PRT
<213> ORGANISM: Tetranychus urticae

<400> SEQUENCE: 1

Met Asn Ser Lys Leu Leu Thr Leu Cys Leu Val Ile Thr Ala Leu Thr
1               5                   10                  15

Ala Val Gln Gln Thr Asn Ala Asn Ser Leu Phe Gly Leu Pro His Met
            20                  25                  30

Lys Ile Gly Leu Gly Asn Met Leu Lys Pro Phe Gly Ile Asp Gly Asn
        35                  40                  45

Ser Gly Ser Lys Ser Ala Ser Ala Ser Thr Ser Lys Ala Thr Ser Gly
    50                  55                  60

His His Thr Gly Ala Gln Ser Ser Pro Pro Ser Gly Pro Pro Ser Leu
65                  70                  75                  80

Ala Ser Gly Asn Gly Ser Ser Gly Ser Gly Ser Ser Ser Ser Ala Thr
                85                  90                  95

Ser Ser Asp Val Gly Pro Asn Lys Pro Ile Asn Ser His Gly Ser Asn
            100                 105                 110

Pro Ser Ser Gly Gln Glu Ser Gly Ser Ser Ser Asn Ile Ser Trp Asn
        115                 120                 125

Ser Gly Ser Ser Thr Ser Ser Tyr Ala Asp Ser Ser Lys Gln Leu Asn
    130                 135                 140

Ser His Gly Ser Thr Thr Ser Ser Gly Ala Ala Ser Gly Ser Gly Ser
145                 150                 155                 160

Ser Gly Ser Gly Ser Ser Gly Ser Ala Ala Ser Gly Ser Ala Ala Ser
                165                 170                 175

Ser Ser Ala Ala Ala Ser Ser Ala Ala Ala Ser Asp Ser Ser Ser Gly
            180                 185                 190

Pro Thr Thr Ser Thr Ser Thr Ser Asn Ser Pro Asn Ser Ala Ser Ser
        195                 200                 205

Gly Ser Gly Ser Gly Ser Ser Ala Ala Ala Ser Ser Gly Ala Ala Ser
    210                 215                 220

Gly Ser Gly Ser Ser Gly Ser Gly Ser Gly Gln Gly Ser Gly Ser Ser
225                 230                 235                 240

Gly Ser Gly Ser Ser Gly Ser Gly Ser Ser Gly Ser Ala Ala Ser Gly
                245                 250                 255

Ser Ala Ala Ser Ser Ser Ala Ala Ala Ala Ala Ser Asp Ser Ser
            260                 265                 270
```

```
Ser Ala Pro Ala Pro Ala Ser Asn Thr Gly Ser Gly Ser Ser Ala
        275                 280                 285

Ala Ser Ser Ser Ala Ala Ala Ser Ser Ala Ala Ala Ser Asp Ser Ser
    290                 295                 300

Ser Gly Pro Thr Ser Gln His Gln Pro Val Asn His Leu Ile Gln His
305                 310                 315                 320

His Gln Asp Gln Val Arg Ile Ile Ser Ser Ser Phe Ile Arg Ser Ser
                325                 330                 335

Ser Gly Ser Ala Ser Ser Ala Ser Gly Ser Gly Gln Ala Ser Gly Ser
            340                 345                 350

Ser Ala Ala Ser Ser Ser Ala Ala Ala Ala Ala Ala Ser Asp Ser Ser
        355                 360                 365

Ser Ala Pro Ala Pro Ala Ser Asn Thr Gly Ser Gly Ser Ser Ser Ala
        370                 375                 380

Ala Ser Ser Ser Ala Ala Ala Ser Ser Ala Ala Ala Ser Asp Ser Ser
385                 390                 395                 400

Ser Gly Pro Thr Thr Ser Thr Ser Thr Ser Asn Ser Pro Asn Ser Ala
                405                 410                 415

Ser Ser Gly Ser Gly Ser Gly Ser Ser Ala Ala Ala Ser Ser Gly Ala
            420                 425                 430

Ala Ser Gly Ser Gly Ser Ser Gly Ser Gly Ser Gly Gln Gly Ser Gly
        435                 440                 445

Ser Ser Gly Ser Gly Ser Ser Gly Ser Gly Ser Ser Gly Ser Ala Ala
        450                 455                 460

Ser Gly Ser Ala Ala Ser Ser Ser Ala Ala Ala Ala Ala Ala Ser Asp
465                 470                 475                 480

Ser Ser Ser Ala Pro Ala Pro Pro Ser Asn Thr Gly Ser Gly Ser Ser
                485                 490                 495

Ser Ala Ala Ser Ser Ser Ala Ala Ala Ser Ser Ala Ala Ala Ser Asp
            500                 505                 510

Ser Ser Ser Gly Pro Thr Thr Ser Thr Ser Thr Ser Asn Ser Pro Asn
        515                 520                 525

Ser Ala Ser Ser Gly Ser Gly Ser Gly Ser Ser Ala Ala Ala Ser Ser
        530                 535                 540

Gly Ala Ala Ser Gly Ser Gly Ser Ser Gly Ser Gly Ser Gly Gln Gly
545                 550                 555                 560

Ser Gly Ser Ser Gly Ser Gly Ser Ser Gly Ser Gly Ser Gly Gln Gly
                565                 570                 575

Ser Gly Ser Ser Gly Ser Gly Ser Ser Gly Ser Gly Ser Ser Gly Ser
            580                 585                 590

Ala Ala Ser Gly Ser Ala Ala Ser Ser Ser Ala Ala Ala Ala Ala Ser
        595                 600                 605

Asp Ser Ser Ser Gly Pro Thr Thr Ser Thr Ser Thr Ser Asn Ser Pro
610                 615                 620

Asn Ser Ala Ser Ser Gly Ser Gly Ser Gly Ser Ser Ala Ala Ala Ser
625                 630                 635                 640

Ser Gly Ala Ala Ser Gly Ser Gly Ser Ser Gly Ser Gly Ser Gly Gln
                645                 650                 655

Gly Ser Gly Ser Ser Gly Ser Gly Ser Ser Gly Ser Gly Ser Ser Gly
            660                 665                 670

Ser Ala Ala Ser Gly Ser Ala Ala Ser Ser Ser Ala Ala Ala Ala Ala
        675                 680                 685

Ala Ser Asp Ser Ser Ser Ala Pro Ala Pro Ala Ser Asn Thr Gly Ser
```

```
                690             695             700
Gly Ser Ser Ala Ala Ser Ser Ala Ala Ser Ser Ala Ala
705             710             715             720

Ala Ser Asp Ser Ser Gly Pro Thr Thr Ser Thr Ser Asn
            725             730             735

Ser Pro Asn Ser Ala Ser Ser Gly Ser Gly Ser Asp Ser Ser Ala
            740             745             750

Pro Ala Pro Ala Ser Asn Thr Gly Ser Gly Ser Ser Ala Ala Ser
            755             760             765

Ser Ser Ala Ala Ala Ser Ser Ala Ala Ala Ser Asp Ser Ser Gly
        770             775             780

Pro Thr Thr Ser Thr Ser Thr Ser Asn Ser Pro Asn Ser Ala Ser
785             790             795             800

Gly Ser Gly Ser Gly Ser Ser Ala Ala Ala Ser Gly Ala Ala Ser
            805             810             815

Gly Ser Gly Ser Ser Gly Ser Gly Ser Gln Gly Ser Gly Ser Ser
            820             825             830

Gly Ser Gly Ser Ser Gly Ser Gly Ser Gly Ser Ala Ala Ser Gly
            835             840             845

Ser Ala Ala Ser Ser Ala Ala Ala Ala Ala Ser Asp Ser Ser
850             855             860

Ser Ala Leu Ser Pro Ala Ser Asn Thr Gly Ser Gly Ser Ser Ala
865             870             875             880

Ala Ser Asp Ser Ser Ser Gly His Thr Thr Ser Thr Ser Thr Ala
            885             890             895

Ser Gly Ser Gly Ser Ser Gly Ser Gly Ser Gly Gln Gly Ser Gly Ser
            900             905             910

Ser Gly Ser Gly Ser Ser Gly Ser Gly Ser Gly Ser Ala Ala Ser
            915             920             925

Gly Ser Ala Ala Ser Ser Ala Ala Ala Ala Ala Ser Asp Ser
            930             935             940

Ser Ser Ala Pro Ala Pro Ala Ser Asn Thr Gly Ser Gly Ser Ser
945             950             955             960

Ala Ala Ser Ser Ala Ala Ala Ser Ser Ala Ala Ala Ser Asp Ser
            965             970             975

Ser Ser Gly Pro Thr Thr Ser Thr Ser Thr Ser Asn Ser Pro Asn Ser
            980             985             990

Ala Ser Ser Gly Ser Gly Ser Gly Ser Ser Ala Ala Ala Ser Ser Gly
            995             1000            1005

Ala Ala Ser Gly Ser Gly Ser Ser Gly Ser Gly Ser Gly Gln Gly
            1010            1015            1020

Ser Gly Ser Ser Gly Ser Gly Ser Ser Gly Ser Gly Ser Ser Gly
            1025            1030            1035

Ser Ala Ala Ser Gly Ser Ala Ala Ser Ser Ala Ala Ala Ala
            1040            1045            1050

Ala Ala Ser Asp Ser Ser Ser Ala Pro Ala Pro Ala Ser Asn Thr
            1055            1060            1065

Gly Ser Gly Ser Ser Ser Ala Ala Ser Ser Ser Ala Ala Ala Ser
            1070            1075            1080

Ser Ala Ala Ala Ser Asp Ser Ser Ser Gly Pro Thr Thr Ser Thr
            1085            1090            1095

Ser Thr Ser Asn Ser Pro Asn Ser Ala Ser Ser Gly Ser Gly Ser
            1100            1105            1110
```

-continued

Gly Ser Ser Ala Ala Ala Ala Ser Gly Ala Ala Ser Gly Ser Gly
    1115                1120                1125

Ser Ser Gly Ser Gly Ser Gly Gln Gly Ser Gly Ser Ser Gly Ser
    1130                1135                1140

Gly Ser Ser Gly Ser Ala Ala Ser Gly Ser Thr Val Pro Ala Tyr
    1145                1150                1155

Leu Lys Tyr Thr Asn Glu Ser Gly Lys Thr Cys Val Cys Tyr
    1160                1165                1170

<210> SEQ ID NO 2
<211> LENGTH: 311
<212> TYPE: PRT
<213> ORGANISM: Tetranychus urticae
<220> FEATURE:
<221> NAME/KEY: misc_feature
<222> LOCATION: (311)..(311)
<223> OTHER INFORMATION: Xaa can be any naturally occurring amino acid

<400> SEQUENCE: 2

Met Arg Thr Leu Gln Ile Leu Leu Val Leu Glu Ile Leu Asp Tyr
1               5                   10                  15

Ala Gln Ser Ala Ser Phe Asp Asp Val Ala Leu Gln Ile Asp Pro Gly
            20                  25                  30

Asn Trp Leu Ile Glu Ala Thr Leu Tyr Asp Gln Ser Asn Asp Glu Arg
        35                  40                  45

Tyr Ser Met Arg Glu Met Ile Tyr Ser Asn Tyr Ser Ile Ser Gly Lys
    50                  55                  60

Leu Ala Ile Thr Ser Asp Ala Gly Ser Phe Asp Ile Phe Tyr His Asp
65                  70                  75                  80

Arg Leu Gln Glu Tyr Arg Leu Val Ile His Asp Asn Arg Cys Asp Thr
                85                  90                  95

Phe Thr Tyr Lys Ser Lys Trp Asp Ser Asn Leu Ser Gly Ile Thr Asn
            100                 105                 110

Pro Leu Leu Asn Arg Ile Leu Leu Val Gly Pro Ser Leu Ile His Arg
        115                 120                 125

Leu Asn Trp Gly Gly His Arg Trp Ile Ser Asp Ser Asp Val Gln Ile
    130                 135                 140

Arg Gly Thr Thr Met His Ser Asp Tyr Ala Asn Met Asn Gly Asn Lys
145                 150                 155                 160

Leu Arg Val Thr Arg Tyr Phe Lys Ser Lys Glu Ala Ile Gln Pro Asp
                165                 170                 175

Arg Ile Val Phe Tyr Gly Thr Asp Val Thr Glu Phe Ser Lys Lys
            180                 185                 190

Gln Ser Phe Ile Met Asp Phe Thr Ser Val Thr Lys Leu Glu Asn Glu
        195                 200                 205

Val Ser Gly Leu Val Thr Val Thr Pro Gly Ile Gly Cys Arg Phe Tyr
    210                 215                 220

Leu Glu Ser Ser Ser Pro Ile Pro Asn Val Pro Ser Asn Gln Leu His
225                 230                 235                 240

Tyr Leu Leu Asp Glu Asn Val Lys Gly Pro Arg Pro Ser Ser Lys Arg
                245                 250                 255

Glu Glu Val Tyr Ala Asp Ile Glu Ala Gln Leu Leu Tyr Arg Lys Met
            260                 265                 270

Thr Ser Gln Gly Lys Glu Glu Glu Thr Ile Tyr Asp Phe Ser Leu Gly
        275                 280                 285

Ile Ser Tyr Lys Leu Leu Asp Lys Gly Tyr Cys Thr Ile Asp Pro Met
    290                 295                 300

```
Ala Ser Ser Asp Pro Gly Xaa
305             310

<210> SEQ ID NO 3
<211> LENGTH: 1112
<212> TYPE: PRT
<213> ORGANISM: Tetranychus urticae

<400> SEQUENCE: 3

Met Val Phe Lys Met Tyr Leu Asn Leu Leu Ile Leu Ala Ile Thr Ala
1               5                   10                  15

Thr Asn Tyr Val Ser Thr Arg Ser Met Gly Ser Met Pro Gly Met Glu
            20                  25                  30

Leu Asp Val Asn Met Pro Met Asp Met Met Ser Asn Val Leu Gly Gly
        35                  40                  45

Ser Ala Phe Ala Gly Ser Asn Ala Asp Thr Glu Asn Glu Gly Ser Glu
    50                  55                  60

Ala Ala Ser Asn Ala Glu Ser Thr Ala Gly Ala Asn Ala Glu Ala Thr
65                  70                  75                  80

Thr Tyr Glu Glu Pro Asp Gly Glu Asp Gly Leu Thr Tyr Gly Asn
                85                  90                  95

Asp Glu Ser Asp Ala Asp Ala Lys Ala Thr Ala Glu Ser Ala Ala Lys
                100                 105                 110

Ala Gly Ser Asp Asn Gly Ser Gly Asn Asn Gly Gly Asn Gly Tyr Gly
            115                 120                 125

Asn Asn Gly Gly Ser Ser Ala Thr Ser Ser Ser Ala Ser Gly
    130                 135                 140

Ser Ser Thr Ser Glu Gly Ser Asp Asn Gly Ser Gly Asn Asn Gly Gly
145                 150                 155                 160

Asn Gly Tyr Asn Asn Gly Asn Asn Gly Gly Ser Ser Ser Ala Thr
            165                 170                 175

Ser Ser Ser Ser Ala Ser Gly Ser Ser Thr Ser Glu Gly Ser Asp Asn
                180                 185                 190

Gly Ser Gly Asn Asn Gly Gly Asn Gly Tyr Asn Asn Asn Gly Asn Asn
            195                 200                 205

Gly Gly Ser Ser Ser Ala Thr Ser Ser Ser Ser Ala Ser Gly Ser Ser
    210                 215                 220

Thr Ser Glu Gly Ser Asp Asn Gly Ser Gly Asn Asn Ala Gly Asn Gly
225                 230                 235                 240

Tyr Asn Asn Asn Gly Asn Asn Gly Gly Ser Ser Ser Ala Thr Ser Ser
                245                 250                 255

Ser Ser Ala Ser Gly Ser Ser Thr Ser Glu Gly Ser Asp Asn Gly Ser
            260                 265                 270

Gly Asn Asn Gly Gly Asn Gly Tyr Gly Asn Asn Gly Gly Ser Ser Ser
        275                 280                 285

Ala Thr Ser Ser Ser Ser Ala Ser Gly Ser Ser Thr Ser Glu Gly Ser
    290                 295                 300

Asp Asn Gly Ser Gly Asn Asn Gly Gly Asn Gly Tyr Asn Asn Asn Gly
305                 310                 315                 320

Asn Asn Gly Gly Ser Ser Ser Ala Thr Ser Ser Ser Ser Ala Ser Gly
                325                 330                 335

Ser Ser Thr Ser Glu Gly Ser Asp Asn Gly Tyr Asn Asn Asn Gly Asn
            340                 345                 350

Asn Gly Gly Ser Ser Ser Ala Thr Ser Ser Ser Ser Ala Ser Ser Ser
        355                 360                 365
```

Ser Thr Ser Glu Gly Ser Asp Asn Gly Ser Gly Asn Gly Gly Asn
    370                 375                 380

Gly Tyr Asn Asn Asn Val Asn Gly Gly Ser Ser Ser Ala Thr Ser
385                 390                 395                 400

Ser Ser Ser Ala Ser Gly Ser Ser Asn Gln Arg Asp Leu Thr Met Val
                405                 410                 415

Ala Val Thr Thr Glu Glu Thr Val Ile Thr Thr Met Val Thr Met Glu
            420                 425                 430

Asp Gln Ala Gln Gln His His Arg Pro Gln His Gln Val His Gln Leu
            435                 440                 445

Gln Arg Asp Leu Thr Thr Val Ala Val Thr Thr Glu Glu Thr Val Ile
    450                 455                 460

Thr Thr Met Val Thr Arg Glu Asp Gln Ala Gln Gln His His His His
465                 470                 475                 480

Gln His Ser Gly Asn Asn Gly Asn Asn Gly Ser Ser Ser Ala Ala Ala
                485                 490                 495

Ser Ser Ala Ala Ala Ala Ser Gly Ser Ser Ala Ser Asn Gly Ser Asp
            500                 505                 510

Asn Asn Gly Gly Asn Asn Gly Asn Asn Gly Ser Ser Ser Ala Ala Ala
            515                 520                 525

Ser Ser Ala Ala Ala Ala Ser Gly Ala Ser Ala Ser Asn Gly Ser Asp
            530                 535                 540

Asn Asn Gly Gly Asn Asn Gly Asn Asn Gly Ser Ser Ser Ala Ala Ala
545                 550                 555                 560

Ser Ser Ala Ala Ala Ala Ser Gly Ser Ser Ala Ser His Gly Ser Asp
                565                 570                 575

Asn Asn Gly Gly Asn Asn Gly Asn Asn Gly Ser Ser Ser Ala Ala Ala
            580                 585                 590

Ser Ser Ala Ala Ala Ser Ser Asp Ala Ser Ala Ser Asn Gly Ser Asp
            595                 600                 605

Asn Asn Gly Gly Asn Asn Gly Asn Asn Gly Ser Ser Ser Ala Ala Ala
    610                 615                 620

Ser Ser Ala Ala Ala Ala Ser Gly Ala Ser Ala Ser Asn Gly Ser Asp
625                 630                 635                 640

Asn Asn Gly Gly Asn Asn Gly Asn Asn Gly Ser Ser Ser Ala Ala Ala
            645                 650                 655

Ser Ser Ala Ala Ala Ala Ser Gly Ser Ser Ala Ser His Gly Ser Asp
            660                 665                 670

Asn Asn Gly Gly Asn Asn Gly Asn Asn Gly Ser Ser Ser Ala Ala Ala
            675                 680                 685

Ser Ser Ala Ala Ala Ser Gly Ser Ser Ala Ser Asn Gly Ser Asp
    690                 695                 700

Asn Asn Gly Gly Asn Asn Gly Asn Asn Gly Ser Ser Ser Ala Ala Ala
705                 710                 715                 720

Ser Ser Ala Ala Ala Ser Gly Ser Ser Ala Ser Asn Gly Ser Asp
                725                 730                 735

Asn Asn Gly Gly His Asn Arg Ser Ser Ser Ala Ala Ala Ala Ser Gly
            740                 745                 750

Ser Ser Ala Ser Asn Gly Ser Asp Asn Asn Gly Gly Thr Asn Gly Asn
            755                 760                 765

Asn Gly Ser Ser Ser Ala Ala Ala Ser Ser Ala Ala Ala Ala Ser Gly
    770                 775                 780

Ser Ser Ala Ser His Gly Ser Asp Asn Asn Gly Gly Asn Asn Gly Asn

```
                785                 790                 795                 800
Asn Gly Ser Ser Ser Ala Ala Ala Ser Ala Ala Ala Ser Gly
                805                 810                 815
Ser Ser Ala Ser Asn Gly Ser Asp Asn Asn Gly Gly Asn Gly Asn
                820                 825                 830
Asn Gly Ser Ser Ser Ala Ala Ala Ser Ala Ala Ala Ser Ser Gly
                835                 840                 845
Ser Ser Ala Ser Asn Gly Ser Asp Asn Asn Gly Gly Asn Gly Asn
                850                 855                 860
Asn Gly Ser Ser Ser Ala Ala Ala Ser Ala Ala Ala Ser Gly
865                 870                 875                 880
Ser Ser Ala Ser Asn Gly Ser Asp Asn Asn Gly Gly Asn Gly Asn
                885                 890                 895
Asn Gly Ser Ser Ser Ala Ala Ala Ser Ala Ala Ala Ser Gly
                900                 905                 910
Ser Ser Ala Ser Asn Gly Ser Asp Asn Asn Gly Gly Asn Gly Asn
                915                 920                 925
Asn Gly Ser Ser Ser Ala Ala Ala Ser Ala Ala Ala Ser Ser Gly
                930                 935                 940
Ser Ser Ala Ser Asn Gly Ser Asp Asn Asn Gly Gly Asn Gly Asn
945                 950                 955                 960
Asn Gly Ser Ser Ser Ala Ala Ala Ser Ala Ala Ala Ser Gly
                965                 970                 975
Ser Asn Ala Lys Lys Asn Asn Gly Ser Asn Ser Gly Ser Asn Ser
                980                 985                 990
Ala Ala Thr Ser Ser Asn Ser Ser Gly Lys Lys Val Asn Asn Ser Gly
                995                 1000                1005
Ser Ser  Ser Gly Ser Ala Ala  Gly Ser Gly Ser Asn  Arg Gly Asn
    1010            1015                1020
Gly Gln  Asn Asn Gly Gly Ser  Lys Gly Ser Asn Gly  Ser Ala Ala
    1025            1030                1035
Ser Ser  Ala Thr Ser Ala Ala  Ala Ala Ser Gly Ala  Ala Gly Asn
    1040            1045                1050
Gly Asn  Ser Lys Lys Gly Ala  Lys Gln Gly Asn Gly  Pro Gly Asn
    1055            1060                1065
Ser Ala  Ala Ser Ala Ser Ala  Ala Ala Ser Ser Ala  Ser Gly Lys
    1070            1075                1080
Gly Ser  Lys Ser Gly Lys Ser  Pro Ala Lys Gln Gly  Ile Ile Pro
    1085            1090                1095
Ala Met  Met Ser Lys Ile Pro  Thr Leu Ser Val Ser  Met Phe
    1100            1105                1110

<210> SEQ ID NO 4
<211> LENGTH: 1026
<212> TYPE: PRT
<213> ORGANISM: Tetranychus urticae
<220> FEATURE:
<221> NAME/KEY: misc_feature
<222> LOCATION: (972)..(1005)
<223> OTHER INFORMATION: Xaa can be any naturally occurring amino acid

<400> SEQUENCE: 4

Met Ile Thr Asn Leu Val Phe Leu Cys Leu Phe Leu Thr Thr Cys Ser
1               5                   10                  15

Leu Ile His Ser Ser His Ser Asn Ser Leu Ser Lys Trp Asn Pro Met
                20                  25                  30
```

-continued

```
Lys Ala Ala Ile Ser Ile Pro Met Lys Met Leu Asp Gly Glu Lys His
             35                  40                  45

Ile His Asn Val Thr Gly Lys Pro His Thr Thr Ala Thr Thr Ser Lys
     50                  55                  60

Pro Gly Ser Ser Gly Ser Ser Gly Ser Ala Ala Ala Ser Asp
 65              70                  75                  80

Ser Ser Ser Gly Pro Thr Ser Asn Gly Asn Ser Ala Asn Ser Ala Ser
                 85                  90                  95

Ser Gly Ser Gly Ser Ser Gly Ser Ser Ala Ala Ser Ser Gly Ala Ser
                100                 105                 110

Gly Ser Gly Ser Ser Gly Ser Gly Ser Gly Gln Gly Ser Ser Ser
            115                 120                 125

Ala Ala Ala Ser Ala Ser Ser Ala Ala Ser Asp Ser Gly Ser Ser
145                 150                 155                 160

Ala Pro Ala Thr Ser Ser Thr Asn Gly Ser Gly Ser Gly Ser Ala Ala
145                 150                 155                 160

Ser Ser Ser Ala Ala Ser Ala Ser Ala Ala Ser Asp Ser Ser
                165                 170                 175

Ser Gly Pro Thr Ser Asn Gly Asn Ser Ala Asn Ser Ala Ser Ser Gly
            180                 185                 190

Ser Gly Ser Ser Gly Ser Ser Ala Ala Ser Ser Gly Ala Ser Gly Thr
            195                 200                 205

Ser Thr Thr Thr Thr Ser Thr Ser Ala Thr Ser Gly Ala Ser Gly Ser
210                 215                 220

Gly Ser Ser Gly Ser Gly Ser Gly Gln Gly Ser Ser Ser Ala Ala
225                 230                 235                 240

Ala Ser Gly Ser Ser Ala Ala Ser Asp Ser Gly Ser Ser Ala Pro
                245                 250                 255

Ala Thr Ser Ser Thr Asn Gly Ser Gly Ser Gly Ser Ala Ala Ser Ser
                260                 265                 270

Ser Ala Ala Ser Ala Ser Ala Ala Ser Asp Ser Ser Ser Gly
            275                 280                 285

Gln Thr Ser Asn Gly Asn Ser Ala Asn Ser Ala Ser Ser Gly Ser Gly
290                  295                 300

Ser Ser Gly Ser Ser Ala Ala Ser Ser Gly Ala Ser Gly Thr Ser Ile
305                 310                 315                 320

Thr Thr Thr Ser Thr Ser Ser Thr Ser Gly Ala Ser Gly Ser Gly Ser
                325                 330                 335

Ser Gly Ser Gly Ser Gly Gln Gly Ser Ser Ser Ala Ala Ala Ser
            340                 345                 350

Gly Ser Ser Ala Ala Ser Asp Ser Gly Ser Ser Ala Pro Ala Thr
            355                 360                 365

Ser Ser Thr Asn Gly Ser Gly Ser Gly Ser Ala Ala Ser Ser Ser Ala
    370                 375                 380

Ala Ser Ala Ser Ala Ala Ala Ser Asp Ser Ser Ser Gly Pro Thr
385                 390                 395                 400

Ser Asn Gly Lys Thr Ala Asn Ser Ala Ser Ser Gly Ser Gly Ser Ser
                405                 410                 415

Gly Ser Ser Ala Ala Ser Ser Gly Ala Ser Gly Thr Ser Thr Thr Thr
            420                 425                 430

Thr Ser Thr Ser Ser Thr Ser Gly Ala Ser Gly Ser Gly Ser Ser Gly
        435                 440                 445

Ser Gly Ser Gly Gln Gly Ser Ser Ser Ser Ala Ser Gly Pro His
            450                 455                 460
```

```
Ala Asn Ser Met Gln Ser Ile Ala Ser Arg Tyr Val Asn Ser Ala Asp
465                 470                 475                 480

Ser Ser Ser Gly Pro Thr Ser Asn Gly Asn Ser Ala Asn Ser Ala Ser
            485                 490                 495

Ser Gly Ser Glu Ser Ser Gly Ser Ser Ala Ala Ser Ser Gly Ala Ser
            500                 505                 510

Gly Thr Ser Thr Thr Thr Thr Ser Thr Ser Ser Thr Ser Gly Ala Ser
        515                 520                 525

Gly Ser Gly Ser Ser Gly Ser Gly Ser Gly Gln Gly Ser Ser Ser Ser
        530                 535                 540

Ala Ala Ala Ser Gly Ser Ser Ala Ala Ser Asp Ser Gly Ser Ser
545                 550                 555                 560

Ala Pro Ala Thr Pro Ser Thr Asn Gly Ser Gly Ser Gly Ser Ala Ala
                565                 570                 575

Ser Ser Ser Ala Ala Ser Ala Ser Ala Ala Ala Ser Asp Ser Ser
                580                 585                 590

Ser Gly Pro Thr Ser Asn Gly Asn Ser Ala Asn Ser Ala Ser Ser Gly
        595                 600                 605

Trp Gly Ser Ser Gly Ser Ser Ala Ala Ser Ser Gly Ala Ser Gly Thr
        610                 615                 620

Ser Thr Thr Thr Thr Ser Thr Ser Ala Thr Ser Gly Ala Ser Gly Ser
625                 630                 635                 640

Gly Ser Ser Gly Ser Gly Ser Gly Gln Gly Ser Ser Ser Ser Ala Ala
            645                 650                 655

Ala Ser Gly Ser Gly Ser Ala Ala Ser Ser Gly Ala Ser Gly Thr Ser
            660                 665                 670

Thr Thr Thr Thr Ser Thr Ser Ser Thr Ser Gly Ala Ser Gly Ser Gly
        675                 680                 685

Ser Ser Gly Ser Gly Ser Gly Gln Gly Ser Ser Ser Ser Ala Ala Ala
        690                 695                 700

Ser Gly Ser Ser Ser Ala Ala Ser Asp Ser Gly Ser Ser Ala Pro Ala
705                 710                 715                 720

Thr Ser Ser Thr Asn Gly Ser Gly Ser Gly Ser Ala Ala Pro Ser Ser
                725                 730                 735

Ala Ala Ser Ala Ser Ala Ala Ala Ser Asp Ser Ser Ser Gly Pro
                740                 745                 750

Thr Ser Asn Gly Asn Ser Ala Asn Ser Ala Ser Ser Gly Ser Gly Ser
        755                 760                 765

Ser Gly Ser Ser Ala Ala Ser Ser Gly Ala Ser Gly Thr Ser Thr Thr
        770                 775                 780

Thr Thr Ser Thr Ser Ser Thr Ser Gly Ala Ser Gly Ser Gly Ser Ser
785                 790                 795                 800

Gly Ser Gly Ser Gly Gln Gly Ser Ser Ser Ser Ala Ala Ala Ser Gly
                805                 810                 815

Ser Ser Ser Ala Ala Ser Gly Ser Gly Ser Ser Ala Pro Ala Thr Ser
            820                 825                 830

Ser Thr Asn Gly Ser Gly Ser Gly Ser Ala Ala Ser Ser Ser Ala Ala
        835                 840                 845

Ser Ala Ser Ala Ala Ala Ser Asp Ser Ser Ser Gly Pro Thr Ser
        850                 855                 860

Asn Gly Asn Ser Ala Asn Ser Ala Ser Ser Gly Ser Gly Ser Ser Gly
865                 870                 875                 880

Ser Ser Ala Ala Ser Ser Gly Ala Ser Gly Thr Ser Thr Thr Thr Thr
```

-continued

```
                    885                 890                 895
Ser Thr Ser Ala Thr Ser Gly Ala Ser Gly Ser Gly Ser Gly Ser
                900                 905                 910

Gly Ser Gly Gln Gly Ser Ser Ser Ala Ala Thr Ser Cys Ser Ser
                915                 920                 925

Ser Ala Ala Ser Asp Ser Gly Ser Ser Ala Pro Ala Thr Ser Ser Leu
                930                 935                 940

Met Asp Gln Asp Gln Asp Gln Gln Leu Gln Val Gln Gln His Gln His
945                 950                 955                 960

Gln Pro Pro Ala Ala Ser Arg Phe Ile Ile Arg Xaa Xaa Xaa Xaa
                965                 970                 975

Xaa Xaa Xaa Xaa Xaa Xaa Xaa Xaa Xaa Xaa Xaa Xaa Xaa Xaa Xaa
                980                 985                 990

Xaa Xaa Xaa Xaa Xaa Xaa Xaa  Xaa Xaa Xaa Xaa Xaa  Arg Ser Pro
                995                 1000                1005

Ile Pro  Asn Leu Phe Trp Asp  Leu Val Gly Phe Pro  Leu Phe Ile
   1010                1015                1020

Gly Ile  Phe
   1025

<210> SEQ ID NO 5
<211> LENGTH: 2271
<212> TYPE: PRT
<213> ORGANISM: Tetranychus urticae

<400> SEQUENCE: 5

Met Phe Lys Leu Thr Leu Val Leu Ile Cys Ile Ser Ala Ile Thr Val
1               5                   10                  15

Ser Glu Gly Arg Ala Val Gln Lys Arg Asn Val Leu Asp Asp Leu Leu
                20                  25                  30

Ala Asn Val Gln Ala Thr Ile Lys Val Glu Asp Asp Gly Lys Leu Ser
            35                  40                  45

Leu Pro Ala Val Gly Gln Ile Glu Arg Ala Arg Ser Ser Phe Leu Glu
        50                  55                  60

Ser Ile Ser Gln Leu Tyr Ala Ala Gln Gln Gly Thr Asp Asn Phe
65                  70                  75                  80

Glu Ser Tyr Leu Pro Asp Leu Gln Lys Ile Leu Ser Gln Arg Val Asp
                85                  90                  95

Ser Val Val Lys Ala Leu Asp Lys His Leu Val Gln Asn Ser Arg Lys
                100                 105                 110

Ile Asp Glu Ile Lys Lys Phe Met Leu Gln Asn Asp Gly Lys Thr Leu
            115                 120                 125

Arg Ser Leu Glu Ser Arg Phe Glu Asn Leu Ile Ser Met Pro Asp Val
        130                 135                 140

Ser Thr Glu Ser Ile Phe Gln Ile Leu Gly Thr Ile Asp Lys Ile Glu
145                 150                 155                 160

Lys His Leu Ile Ser Glu Val Ser Ser Leu Lys Ser Arg Gly Leu Phe
                165                 170                 175

Gly Ile Asn Trp Gly Ser Val Lys Asp Thr Val Val Asp Arg Gly Thr
                180                 185                 190

Ala Ile Ala Glu Lys Val Gly Asp Thr Ile Arg Cys Phe Phe Gly Ile
            195                 200                 205

Gly Cys Gly Asn Arg Lys Ser Lys Ala Asp Glu Glu Lys Asp Gln Lys
        210                 215                 220

Lys Arg Gln Glu Glu Glu Glu Lys Lys Arg Lys Gln Gln Glu Lys Ile
```

```
                225                 230                 235                 240
Glu Lys Glu Lys Glu Asn Val Arg Ala Ala Leu Glu Lys Val Glu Lys
                    245                 250                 255
Ala Asp Arg Leu Ser Asn Glu Glu Lys Ile Asp Thr Phe Arg Gln Ala
                260                 265                 270
Ser Ala Ala Leu Asp Lys Ala Glu Asn Ser Ala Asp Gln Val Ile Lys
            275                 280                 285
Glu Val Lys Ser Asn Ser Pro Thr Lys Asn Gly Ser Ser Ala Ser Ser
        290                 295                 300
Ser Ser Lys Thr Asn Thr Lys Pro Thr Ser Asn Ser Glu Lys Asn Thr
305                 310                 315                 320
Lys Ser Gln Ser Gln Ala Gln Pro Val Thr Leu Lys Pro Asp Lys Thr
                325                 330                 335
Lys Glu Thr Asp Asn Ser Lys Lys Thr Ser Ser Pro Gln Lys Gln Ser
                340                 345                 350
Gln Ser Ser Gly Pro Ser Ala Ala Lys Lys Pro Val Asp Ser Lys Lys
            355                 360                 365
Asp Leu Ser Pro Gln Lys Gln Ser Glu Ser Ser Gly Val Gln Leu
        370                 375                 380
Val Val Asp Leu Pro Val Ser Ala Ser Gln Asn Thr Asn Ser Gly Thr
385                 390                 395                 400
Ser Asn Asp Lys Lys Ser Gly Pro Ser Thr Lys Gln Thr Ala Glu Pro
                405                 410                 415
Lys Lys Glu Ser Glu Ala Ser Lys Gln Ser Lys Ala Val Glu Ser Lys
                420                 425                 430
Lys Gly Ser Ser Pro Gln Lys Gln Ser Glu Ser Ser Gly Ala Gln
            435                 440                 445
Leu Ile Val Asp Leu Pro Val Ser Thr Ser Asn Thr Asn Ser Gly
        450                 455                 460
Ala Ser Asn Glu Lys Lys Ser Glu Ser Ser Thr Lys Gln Thr Ala
465                 470                 475                 480
Glu Pro Lys Lys Asp Ala Ser Ser Gln Lys Gln Ser Glu Pro Ser Ser
                485                 490                 495
Ser Ala Gln Asn Ala Glu Pro Lys Lys Asp Val Glu Ser Ser Lys Gln
                500                 505                 510
Ser Gln Ala Thr Glu Ser Lys Lys Asp Ser Ser Pro Gln Lys Gln Ser
            515                 520                 525
Asp Ser Ser Ser Gly Val Gln Leu Val Val Asp Ala Pro Val Ser Thr
530                 535                 540
Ser Leu Asp Thr Asn Ser Gly Thr Ser Asn Asp Lys Lys Ser Ser Asp
545                 550                 555                 560
Ser Thr Ser Asp Pro Ser Ala Thr Lys Gln Thr Ala Glu Ser Lys Lys
                565                 570                 575
Asp Ser Ser Gly Val Gln Leu Val Val Asp Leu Pro Val Ser Ser
            580                 585                 590
Ser Gln Asn Thr Asn Ser Gly Thr Ser Asn Asn Lys Lys Ser Glu Pro
        595                 600                 605
Ser Ser Glu Pro Ser Ser Thr Lys Gln Thr Val Glu Pro Thr Lys Gly
    610                 615                 620
Ser Glu Ser Ser Lys Gln Ser Glu Ala Ser Thr Lys Gln Asn Asp Glu
625                 630                 635                 640
Leu Thr Lys Asp Ser Ala Pro Gln Lys Gln Ser Asn Ser Ser Gly
            645                 650                 655
```

```
Val Gln Leu Val Val Asp Thr Pro Val Ser Asn Ser Gln Asp Thr Arg
            660                 665                 670

Ser Gly Asn Ser Asn Asp Lys Lys Ser Ser Asp Ser Ser Ser Glu Pro
            675                 680                 685

Ser Ser Thr Lys Gln Thr Val Glu Pro Thr Lys Asp Ser Glu Ser Ser
    690                 695                 700

Lys Gln Ser Gln Ala Ser Glu Ser Lys Lys Asp Ser Ser Ser Gly Val
705                 710                 715                 720

Gln Leu Val Val Asp Thr Pro Val Ser Ser Gly Ser Ser Asp Arg Asn
                725                 730                 735

Gln Pro Thr Asp Thr Lys Lys Asp Val Asp Ser Ser Glu Lys Thr His
            740                 745                 750

Asn Ser Glu Ser Lys Ile Asn Glu His Glu Thr Ser Thr Lys His Ser
        755                 760                 765

Asp Leu Tyr Ser Gln Thr Val Thr Gln Ala Trp Asn Ala Glu Ser Leu
    770                 775                 780

Ser Ala Gly Gln Asp His Thr Thr Lys Pro Asn Ala Ser Leu Ser Asp
785                 790                 795                 800

Glu Thr Ala Val Glu Phe Ser Ser Asp Ser Tyr Glu Asp Val Thr Val
                805                 810                 815

Gly Ser Ala Ala Ser Ser Glu Thr Ser Asn His Gly Ser Ile Ser Val
            820                 825                 830

Ala Ala Thr Ser Glu Ala Asn Gln Pro Thr Thr Gln Ser Thr Asn Ser
        835                 840                 845

Ser Thr Ser Asp Gly Asn Lys Val Val Ile Ile Thr Ser Asn Asp
    850                 855                 860

Asn Asp Ser Gly Ser Ser Glu Ile Pro Ser Gln Ser Ser Asn Gln Gln
865                 870                 875                 880

Thr Ser Ser Asn Ser Ala Ser Ala Thr Asn Asn Gln Thr Ser Gln Glu
                885                 890                 895

Ser Ser Ser Thr Ile Thr Ser Val His Asp Gly Val Asn Ala Gly Ser
            900                 905                 910

Asp Gln Ala Lys Asp Gln Ser Gly Ser Pro Ser Ser Gln Thr Ser Asn
        915                 920                 925

His Glu Ser Ser Leu Ser Ser Thr Ser Glu Ser Thr Thr Gln Ser Ser
    930                 935                 940

Gln Ala Ser Tyr Glu Ser Ser Ile Arg Thr Ser Asp Thr Glu Ser
945                 950                 955                 960

Asn Ser Pro Val Thr Gln Gln Ser Gly Gly Leu Ser Ile Asp Val Thr
                965                 970                 975

Val Gly Ser Ile Val Pro Val Ser Thr Glu Thr Lys Cys Arg Asn Arg
            980                 985                 990

Asp Pro Gln Met Lys Asn Asp Ser Ala Ser Ser Val Gln Ala Ser Gln
        995                 1000                1005

Glu Ser Asn Ser Thr Val Ala Ser Leu Tyr Val Asp Ser Thr Val
    1010                1015                1020

Gly Ser Ala Val Thr Glu Asn Gln Ser Val Ser Gln Thr Ser Thr
    1025                1030                1035

Ser Ser Leu Glu Tyr Ser Thr Gln Ala Ser Ser Gln Glu Ser Gly
    1040                1045                1050

Glu Ile Arg Thr Ser Asp Ser Glu Ser Ser Asn Pro Leu Ser Gln
    1055                1060                1065

Gln Ser Ser Glu Val Ser Ile Asp Val Thr Val Gly Ser Val Asp
    1070                1075                1080
```

```
Ser Val Ala Thr Glu Thr Ser Ser Gln Ala Ser Gln Thr Ser Ser
1085                1090                1095

Gln Ser Ser Ser Asn Val Ser Val Ser Val Ser Ile Thr Ser Glu
1100                1105                1110

Gly Asn Glu Pro Thr Thr Ser Asn Thr Ser Asp Gly Asn Thr Val
1115                1120                1125

Val Ile Val Thr Thr Asn Asp Asn Asp Phe Gly Ser Ala Gly Thr
1130                1135                1140

Ser Ser Gln Ser Ser Ser His Gln Asp Val Ser Ser Leu Asn Glu
1145                1150                1155

His Pro Thr Glu Ser Gln Asp Leu Thr Thr Thr Ser Glu Ser Leu
1160                1165                1170

Ser Asp Glu Ile Asp Phe Glu Phe Ser Thr Asp Ser Tyr Glu Glu
1175                1180                1185

Val Thr Val Gly Ser Ser Ala Ser Ser Ala Thr Ser Asn Tyr Glu
1190                1195                1200

Ser Gln Ser Ser Asn His Glu Ser Val Ser Val Ser Ala Thr Thr
1205                1210                1215

Gln Ser Asn Glu Pro Thr Thr Ser Asn Ser Ala Asp Gly Asn Thr
1220                1225                1230

Val Val Val Val Val Ala Thr Asn Gln Asn Asp Ser Ala Ser Ser
1235                1240                1245

Gly Thr Pro Ser Gln Ser Ala Asn Gln Gln Thr Ser Ser Ser Ser
1250                1255                1260

Ser Ser Ala Thr Asn Ser Gln Ala Ser Gln Glu Ser Asn Pro Thr
1265                1270                1275

Val Ala Ser Leu Tyr Glu Asp Ser Ile Val Gly Ser Ala Val Thr
1280                1285                1290

Glu Asn Gln Ser Val Ser Gln Thr Ser Thr Ser Ser Ser Glu Tyr
1295                1300                1305

Ser Thr Gln Ala Ser Ser Gln Glu Ser Gly Ala Lys Arg Thr Ser
1310                1315                1320

Asp Ser Glu Ser Ser Asn Pro Val Ser Gln Gln Ser Ser Glu Val
1325                1330                1335

Ser Ala Asp Val Thr Val Gly Ser Ile Val Pro Val Ser Thr Glu
1340                1345                1350

Thr Ser Ser Gln Ala Val Gln Thr Ser Ser Gln Ser Ser Ser Asn
1355                1360                1365

Val Ser Ala Ser Val Ser Ser Glu Val Asn Glu Pro Thr Thr Ser
1370                1375                1380

Ser Thr Ser Asp Gly Asn Thr Val Val Val Ile Val Ser Ser Asn
1385                1390                1395

Glu Asn Ser Glu Val Ser Ser Ser Gln Ser Ala Ser His Glu Ser
1400                1405                1410

Lys Pro Ser Asp Asp Ser Val Ser Gln Ser Val Thr Pro Ala Trp
1415                1420                1425

Asn Ser Ala Ser Leu His Glu Gly Gln Asp Leu Thr Thr Ser Ser
1430                1435                1440

Glu Ser Leu Ser Asp Glu Ile Ala Phe Glu Phe Ser Thr Asp Ser
1445                1450                1455

Tyr Glu Asp Ala Thr Val Gly Ser Ser Ala Ser Ser Ser Ile Ser
1460                1465                1470

Val Ser Thr Thr Ser Glu Gly Asn Glu Pro Thr Thr Gln Ala Thr
```

```
                    1475                1480                1485

Ser Ser Thr Ser Asp Gly Asn Thr Val Val Ile Val Thr Thr
    1490                1495                1500

Asn Glu Asn Glu Ser Gly Ser Ser Ser Ala Pro Ser Gln Thr Ser
    1505                1510                1515

Ser Gln Gln Thr Asn Ser Gly Ser Ala Ala Asn Asn Gln Ala Ser
    1520                1525                1530

Gln Glu Ser Asn Pro Thr Val Ala Ser Asn Phe Asp Ser Ile Ser
    1535                1540                1545

Glu Val Gln Ser Thr Gln Ser Ser Ala Ser Ser Ser Tyr Asp Asp
    1550                1555                1560

Thr Thr Val Gly Ser Ser Glu Ala Val Val Gln Ser Thr His Lys
    1565                1570                1575

Met Pro Thr Gln Asp Ser Thr Pro Ser Ser Ser Thr Gln Ser Thr
    1580                1585                1590

Ser Asn Ser Asp Ser Glu Ser Ser Asn Pro Val Thr Gln Gln Ser
    1595                1600                1605

Gly Gly Val Ser Ile Asp Val Thr Val Gly Ser Val Asp Ser Val
    1610                1615                1620

Ser Thr Glu Thr Ser Ser Gln Ala Ser Gln Thr Ser Ser Gln Ser
    1625                1630                1635

Thr Ser Asn Thr Ala Asn Ser Ala Ala Gly Ser Ser Gly Ala Asp
    1640                1645                1650

Ala Val Val Val Phe Val Thr Ser Thr Glu Ala Thr Thr Gly Ser
    1655                1660                1665

Phe Gly Ile Pro Ser Gln Ser Thr Ser Ser Ser Ser Ser Ser Ser
    1670                1675                1680

Ser Glu Ile Asn Asn Gln Ser Ser Glu Gln Lys Tyr Glu Ser Ser
    1685                1690                1695

Ser Ser Glu Thr Ile Thr Gln Ala Trp Asn Ser Gly Ser Leu Ala
    1700                1705                1710

Val Glu Gln Asp Asn Thr Asn Ala Ser Gly Gly Leu Ser Asp Gly
    1715                1720                1725

Thr Val Phe Glu Phe Ser Thr Asp Ser Tyr Glu Asp Gln Thr Val
    1730                1735                1740

Gly Ser Val Val Thr Gln Asp Gln Ser Val Ser Pro Thr Ser Ser
    1745                1750                1755

Ser Ser Ser Glu Tyr Ser Thr Gln Ser Ser Gln Ser Ser Gln Gln
    1760                1765                1770

Ser Glu Ser Thr Arg Asn Ser Asn Ser Glu Pro Ser Asn Pro Val
    1775                1780                1785

Thr Gln Gln Ser Asp Glu Val Ser Ile Asp Val Thr Val Gly Ser
    1790                1795                1800

Val Ser Thr Glu Ser Gln Asp Pro Gln Thr Ser Ser Gln Ser Ser
    1805                1810                1815

Ser Asn Val Ser Ile Ser Val Ser Thr Ser Ser Glu Gly Asn Glu
    1820                1825                1830

Pro Thr Thr Gln Ala Thr Ser Ser Lys Ser Asp Gly Asn Thr Val
    1835                1840                1845

Val Val Ile Val Thr Thr Asn Asp Ser Ala Ser Ser Gly Thr Pro
    1850                1855                1860

Ser Gln Thr Ser Asn Gln Gln Thr Ser Ser Ser Ser Ser Ser Val
    1865                1870                1875
```

```
Ile Asn Asn Gln Ala Ser Gln Glu Asn Arg Pro Thr Val Ala Ser
    1880            1885                1890

Thr Phe Asp Phe Ile Ser Glu Ala Pro Ser Thr Gln Ser Ser Ser
    1895            1900                1905

Ser Pro Ser Tyr Asp Asp Thr Val Gly Ser Ser Glu Val Val
    1910            1915                1920

Asp Gln Ser Thr Ser Gln Thr Ser Ser Gln Asn Thr Thr Pro Ser
    1925            1930                1935

Ser Ser Val Glu Ser Gly Ser Ile Arg Asn Ser Asp Ser Asp Ser
    1940            1945                1950

Gln Ser Tyr Ser Pro Val Thr Gln Gln Ser Gly Glu Val Ser Ile
    1955            1960                1965

Asp Val Thr Val Gly Ser Val Asp Ser Val Ser Thr Glu Thr Ser
    1970            1975                1980

Ser Gln Ser Thr Gln Thr Ser Ser Gln Ser Ser Ser Asn Val Ser
    1985            1990                1995

Val Ser Val Ser Thr Ala Ser Glu Gly Asn Glu Pro Thr Thr Ser
    2000            2005                2010

Ala Ser Ser Ser Ser Ala Gln Ser Gly Thr Gln Ser Ser Gln Glu
    2015            2020                2025

Ser Gly Ser Ile Arg Thr Ser Asp Ser Glu Ser Ser Asn Pro Val
    2030            2035                2040

Thr Gln Gln Ser Ser Ala Ile Asp Ile Asp Val Thr Val Gly Ser
    2045            2050                2055

Val Asp Ser Val Ser Ser Glu Thr Ser Ser Gln Ala Ser Gln Thr
    2060            2065                2070

Ser Ser Gln Ser Thr Ser Asn Thr Ala Asn Ser Ser Ala Gly Ser
    2075            2080                2085

Ser Gly Val Asp Ala Val Val Val Phe Val Thr Ser Thr Glu Ala
    2090            2095                2100

Thr Thr Val Tyr Gln Ser Gly Ser Ser Ser Ser Ser Ser Ser Ser
    2105            2110                2115

Ala Ser Phe His Phe Thr Asn Gln Thr Ser Gln Val Asn Glu Asp
    2120            2125                2130

Asn Glu Pro Ala Val Ser Thr Glu Thr Ile Gln Val Asp Gln Thr
    2135            2140                2145

Ser Thr Gln Ser Ser Ser Gln Glu Ala Val Ser Thr Ser Ser Ala
    2150            2155                2160

Ser Ser Glu Thr Lys Asn Pro Val Thr Gln Pro Ala Val Asp Thr
    2165            2170                2175

Ser Ser Ser Glu Ser Ser His Ala Phe Asp Glu Ile Thr Arg Val
    2180            2185                2190

Ser Thr Pro Leu Glu Ser Ile Thr Glu Ala Val Asn Glu Val Asn
    2195            2200                2205

Asn Glu Ser Asp Ser Thr Glu Ala Ser Gln Ile Thr Ser Thr Gly
    2210            2215                2220

Asn Ala Ser His Asn His Thr Leu Tyr Val Ala Val Lys Val Ser
    2225            2230                2235

Ser Thr Glu Pro Ile Val Ala Ser Ser Val Ala Lys Lys Val Lys
    2240            2245                2250

Thr Val Leu Ser Ser Ser Ser Asn Ser Ala Asp Val Val Val Ile
    2255            2260                2265

Pro Ala Ala
    2270
```

<210> SEQ ID NO 6
<211> LENGTH: 337
<212> TYPE: PRT
<213> ORGANISM: Tetranychus urticae

<400> SEQUENCE: 6

```
Met Ile Arg Ala Ala Leu Phe Ile Ala Leu Phe Ala Leu Ala Thr Ala
1               5                   10                  15

Ala Asn Leu Ser Leu Asp Ser Gln Trp Glu Ser Phe Lys Ile Lys Tyr
                20                  25                  30

Gly Lys Ser Tyr Glu Ser Glu Ala Glu Glu Thr Tyr Arg Arg Ser Val
            35                  40                  45

Phe Ala Lys Lys Met Glu Lys Ile Lys Ala His Asn Glu Arg Ala Asp
    50                  55                  60

Asn Gly Glu Val Thr His Arg Lys Gly Ile Asn Lys Phe Ser Asp Leu
65                  70                  75                  80

Thr Thr Glu Glu Phe Lys Ala Lys His Leu Gly Leu Thr Ala Lys His
                85                  90                  95

His Gly Ser Arg Ser Ile Val Arg Arg Ser Ala Pro Leu Ile His Asn
            100                 105                 110

Ala Asn Asn Thr Val Lys Ala Ala Ala Tyr Val Asp Trp Arg Thr Lys
    115                 120                 125

Gly Ile Val Ser Gln Val Lys Glu Gln Gln Asp Cys Gly Ala Cys Trp
130                 135                 140

Ala Phe Ser Ala Ile Ala Ala Ile Glu Ala Ala Asn Ala Gln Lys Thr
145                 150                 155                 160

Gly Lys Leu Val Glu Leu Ser Val Gln Asn Val Leu Asp Cys Ser Trp
                165                 170                 175

Asn Tyr Ser Ser Leu Gly Cys Ala Gly Gly Trp Ile Asn Tyr Ala Phe
            180                 185                 190

Ser Tyr Val Lys Asp Asn Lys Gly Ile Asp Thr Glu Lys Ser Tyr Pro
    195                 200                 205

Tyr Ile Ser Gly Asp Gly Ile Asp Tyr His Thr Cys Arg Tyr Asn Glu
    210                 215                 220

Ser Asn Lys Gly Ala Ser Ile Ala Ser Phe Val Asp Ile Pro Glu Gly
225                 230                 235                 240

Asp Glu Glu Ala Leu Leu Ala Ala Val Ala Glu His Val Val Ala Val
                245                 250                 255

Gly Ile Asp Ala Ala Ser Val Tyr Glu Tyr Gly Ser Gly Ile Tyr Tyr
            260                 265                 270

Thr Asp Glu Cys Ser Ser Asp Pro Lys Asp Asn Asn His Ala Val Ala
    275                 280                 285

Val Val Gly Tyr Gly Ser Glu Asn Gly Ile Pro Phe Trp Ile Ile Lys
    290                 295                 300

Asn Ser Trp Gly Met Leu Phe Gly Glu Ser Gly Tyr Phe Arg Leu Tyr
305                 310                 315                 320

Arg Gly Ser Asn Met Cys Gly Ile Ala Asn Gly Ala Ser Tyr Pro Ile
                325                 330                 335

Val
```

<210> SEQ ID NO 7
<211> LENGTH: 317
<212> TYPE: PRT
<213> ORGANISM: Tetranychus urticae

<400> SEQUENCE: 7

```
Met Gly Ile Ile Gln Gly Asp Ser Tyr Ser Cys Phe Phe Val Leu Gln
1               5                   10                  15

Thr Lys Tyr Gly Lys Ser Tyr Glu Ser Asn Val Glu Glu Thr Tyr Arg
            20                  25                  30

Arg Ser Val Phe Ala Gln Lys Met Glu Leu Ile Lys Ala His Asn Glu
        35                  40                  45

Arg Ala Asn Asn Gly Glu Phe Thr Tyr Arg Lys Gly Ile Asn Lys Phe
    50                  55                  60

Ser Asp Leu Thr Thr Glu Glu Phe Lys Ala Lys Tyr Leu Gly Phe Lys
65                  70                  75                  80

Ala Thr Ala Arg Arg Ile Ala Pro Phe Ile Tyr Lys Val Asn Lys Thr
                85                  90                  95

Val Lys Ala Pro Thr Leu Val Asp Trp Arg Thr Lys Gly Ile Val Ser
            100                 105                 110

Glu Val Lys Glu Gln Gln Glu Cys Gly Ala Cys Trp Ala Phe Ser Ala
        115                 120                 125

Ile Ala Ala Ile Glu Ala Ala Asn Ala Gln Lys Thr Gly Lys Leu Val
    130                 135                 140

Val Leu Ser Glu Gln Asn Val Leu Asp Cys Ser Trp Lys Tyr Gly Asp
145                 150                 155                 160

Gln Gly Cys Gly Gly Gly Tyr Met Asp Asp Ala Phe Leu Tyr Val Lys
                165                 170                 175

Asp Asn Asn Gly Val Asp Thr Glu Lys Ser Tyr Pro Tyr Ile Ser Gly
            180                 185                 190

Asp Gly Gln Asp Tyr His Thr Cys Arg Tyr Asn Glu Ser Asn Lys Gly
        195                 200                 205

Ala Ser Ile Ala Ser Phe Val Asp Ile Pro Glu Gly Asp Glu Glu Ala
    210                 215                 220

Leu Leu Ser Ala Val Ser Glu His Val Val Ala Val Ala Ile Asp Val
225                 230                 235                 240

Gly Pro Leu His Asp Tyr Glu Ala Gly Ile Leu Asn Thr Asn Glu Cys
                245                 250                 255

Ser Ser Asp Pro Lys Asp Leu Ser His Ala Val Ala Val Val Gly Tyr
            260                 265                 270

Gly Ser Glu Asn Gly Ile Pro Phe Trp Ile Val Arg Asn Ser Trp Gly
        275                 280                 285

Gln Asp Phe Gly Glu Ser Gly Tyr Phe Arg Leu Tyr Arg Gly Ser Asn
    290                 295                 300

Met Cys Gly Ile Ala Asn Leu Ala Ser Tyr Pro Ile Val
305                 310                 315
```

<210> SEQ ID NO 8
<211> LENGTH: 226
<212> TYPE: PRT
<213> ORGANISM: Tetranychus urticae

<400> SEQUENCE: 8

```
Ala Ser Gly Ala Ser Ser Asn Gly Ser Asp Asn Gly Gly Asn Asn
1               5                   10                  15

Gly Asn Asn Gly Ser Ser Ser Ala Ala Ala Ser Ser Ala Ala Ala
            20                  25                  30

Ala Ser Gly Ala Ser Ser Asn Gly Ser Asp Asn Gly Gly Asn Asn
        35                  40                  45

Gly Asn Asn Gly Ser Ser Ser Ser Ala Ala Ala Ser Ser Ala Ala Ala
```

```
            50                  55                  60
Ala Ser Gly Ala Ser Ser Asn Gly Ser Ser Lys Asn Ala Gly Asn Ser
 65                  70                  75                  80

Gly Asn Asn Gly Ala Ser Ser Ala Ala Gly Ser Ala Ser Asn Gly
                 85                  90                  95

Ser Asn Lys Asn Gly Asn Ala Gly Asn Asn Ser Gly Ala Ser Ser Ala
                100                 105                 110

Ala Gly Ser Ser Asn Gly Ser Gly Gln Lys Val Asn Ser Gly Ser
                115                 120                 125

Ser Thr Thr Ala Gly Ser Gly Asn Asn Gly Asn Gly Gln Lys Ser
            130                 135                 140

Gly Gln Ala Val Ser Asn Gly Ser Ala Ala Ser Ser Ala Ala Ala
145                 150                 155                 160

Ser Ala Gly Asn Gly Asn Ala Lys Lys Gly Lys Gln Gly Asn Gly
                165                 170                 175

Lys Gly Asn Ala Ala Ala Ala Ala Ala Ala Ser Ser Ser Ser
                180                 185                 190

Gly Asn Gly Ser Lys Ser Gly Lys Asn Pro Ser Lys Gln Gly Ile Ile
                195                 200                 205

Pro Ala Met Met Ser Lys Ile Pro Val Thr Met Pro Leu Thr Val Ser
210                 215                 220

Leu Phe
225

<210> SEQ ID NO 9
<211> LENGTH: 707
<212> TYPE: PRT
<213> ORGANISM: Tetranychus urticae

<400> SEQUENCE: 9

Met Lys Tyr Lys Lys Asn Phe Leu Arg Lys Asn Tyr Ile Ile Ser
 1               5                  10                  15

Thr Phe Glu Lys Lys Thr Val Lys Phe Glu Lys Thr Phe Lys Met Val
                 20                  25                  30

Lys Asn Met Tyr Ser Cys Leu Val Leu Leu Ala Ile Ile Ser Cys Asn
             35                  40                  45

Tyr Val Ser Met Gln Leu Glu Val Val Gly Ser Val Met Ser Gly Val
         50                  55                  60

Pro Gly Leu Thr Ser Met Glu Lys Ser Val Pro Asp Gly Gly Ser Thr
 65                  70                  75                  80

Ala Asn Ala Ile Ser Glu Ala Gln Ala Thr Ala Gly Asn Val Asp Gly
                 85                  90                  95

Gly Met Gly Ser Leu Glu Asp Ser Pro Ala Gly Asp Leu Leu Asp
                100                 105                 110

Val Glu Leu Asn Met Pro Asn Pro Phe Asp Gly Ser Pro Asp Asp Thr
            115                 120                 125

Asp Asp Ser Pro Ser Asp Asn Asp Asp Gly Gly Leu Met Pro Gly
130                 135                 140

Val Pro Ala Pro Met Pro Gly Ala Pro Ala Ser Met Pro Ser Val Pro
145                 150                 155                 160

Thr Thr Asp Ser Val Asn Ser Ile Val Gly Ser Ile Ala Asn Ala Met
                165                 170                 175

Ala Ser Ala Lys Ser Lys Ser Gly Ser Gly Val Ser Gln Glu Asn Gly
                180                 185                 190

Gly Ser Asn Gly Gly Ser Gly Ser Gly Val Glu Thr Gly Ala Ser Ser
```

```
                195                 200                 205
Val Ala Glu Ser Asn Ala Asp Asn Ser Gly Ala Val Thr Asn Thr
210                 215                 220

Asn Asn Asp Ser Ser Ser Asp Ser Ser Val Ala Thr Ser Ser Thr
225                 230                 235                 240

Asp Thr Asn Asn Ser Asn Asn Val Ser Asn Ala Lys Ala Val Ser
                245                 250                 255

Ser Thr Asn Asn Glu Ala Thr Ser Asn Asp Val Ser Asn Thr Asn Thr
                260                 265                 270

Gly Ser Ser Asn Asn Ser Gln Ser Asn Asn Ser Val Ser Asn Thr
                275                 280                 285

Glu Ala Val Ser Ser Ser Asn Thr Glu Ser Asn Thr Asn Asn Glu Ser
290                 295                 300

Asn Asn Asp Asn Arg Ser Asn Ser Asn Ala Val Ser Asn Ala Asn Ala
305                 310                 315                 320

Val Ser Ser Ser Asn Ser Lys Ser Ser Asn Asn Asn Glu Ala Thr Ser
                325                 330                 335

Asn Asp Val Ser Asn Thr Asn Thr Gly Ser Ser Asn Asn Ser Gln Ser
                340                 345                 350

Asn Asn Asn Ser Val Ser Asn Ala Asn Ala Val Ser Ser Ser Asn Ala
                355                 360                 365

Glu Ser Asn Thr Asn Asn Glu Ser Asn Asn Asp Asn Arg Ser Asn Ser
370                 375                 380

Asn Ala Val Ser Asn Ala Asn Ala Val Ser Ser Asn Ser Lys Ser
385                 390                 395                 400

Ser Asn Asn Asn Val Ser Asn Val Ser Asn Thr Asn Asn Glu Ser Thr
                405                 410                 415

Ser Asn Thr Asn Ser Val Ser Asn Thr Asn Thr Glu Ser Asn Ser Asn
                420                 425                 430

Ser Ala Ala Lys Thr Gly Gly Ser Ser Gly Thr Gly Asn Ser Gly Gly
                435                 440                 445

Ser Ser Ser Val Ser Ser Ser Ser Ser Gly Ser Gly Ala Ala Ser Ser
450                 455                 460

Ser Gly Ser Gly Ala Gly Ser Gly Ser Gly Ala Gly Ser Gly
465                 470                 475                 480

Ser Gly Ala Gly Ser Gly Ser Gly Ser Gly Ala Gly Ser Gly
                485                 490                 495

Ser Gly Ala Gly Ser Gly Ser Gly Ser Gly Ser Gly Ser Gly
                500                 505                 510

Ala Gly Ser Gly Ser Gly Ser Gly Ser Gly Ser Gly Ser Ala Gly
                515                 520                 525

Ser Gly Ser Gly Ser Gly Ser Gly Ser Gly Ala Gly Ser Gly
                530                 535                 540

Ser Gly Ala Gly Ser Gly Ser Gly Ala Gly Ser Gly Ser Gly Ser Gly
545                 550                 555                 560

Ser Gly Ala Gly Ser Gly Ser Gly Ala Gly Ser Gly Ser Gly Ser Gly
                565                 570                 575

Ser Gly Ser Gly Ser Gly Ala Gly Ser Gly Ser Gly Ser Gly Ser Gly
                580                 585                 590

Ser Gly Ser Gly Ala Gly Ser Gly Ser Gly Ala Gly Ser Gly Ser Gly
                595                 600                 605

Ser Gly Lys Gly Asn Gly Asn Ser Gly Gly Ser Ser Pro Gly Thr Ala
                610                 615                 620
```

```
Ser Ser Ala Ser Ser Ser Ser Ser Ser Ala Ser Gly Ala Gly
625                 630                 635                 640

Lys Gly Lys Gly Lys Asn Gly Lys Gly Lys Gly Pro Lys Gly Gly Ser
                645                 650                 655

Ser Ala Ser Ser Ala Ala Ala Ala Ala Ala Ser Ala Ala Ser Lys
        660                 665                 670

Gly Lys Pro Asn Gly Lys Gly Asn Ser Gly Ser Gly Ser His Ser Thr
        675                 680                 685

Lys Lys Pro Met Ile Lys Val Asp Met Pro Met Val Gly Met Lys Val
690                 695                 700

Asn Met Leu
705

<210> SEQ ID NO 10
<211> LENGTH: 340
<212> TYPE: PRT
<213> ORGANISM: Tetranychus urticae

<400> SEQUENCE: 10

Met Ile Tyr Leu Ile Phe Pro Phe Ile Leu Leu Ser Leu His Leu Ser
1               5                   10                  15

Pro Ile Gln Ser Ile Glu Leu Ser Glu Asn Glu Leu Asp Ser Tyr Trp
            20                  25                  30

Thr Thr Tyr Lys Val Arg His Gly Lys Asn Tyr Thr Phe Ser Ala Asp
        35                  40                  45

Asp Tyr Phe Arg Lys Tyr Ala Phe Gly Met Asn Leu Asn Lys Ile Leu
    50                  55                  60

Lys His Asn Thr Val Ala Asp Leu Gly Leu Arg Asn Phe Lys Leu Ser
65                  70                  75                  80

Leu Asn Arg Tyr Ala Asp Lys Thr Thr Gly Glu Met Val Lys Gln Arg
                85                  90                  95

Thr Gly Leu Ser Ser Thr Ser Leu Lys Ser Ala Gln Leu Lys Leu Phe
            100                 105                 110

Lys Pro Arg Leu Thr Asp Ala Asn Val Thr Ser Asp Lys Gly Ser Ser
        115                 120                 125

Phe Asp Trp Arg Ser His Gly Ile Val Asn Pro Val Asp Gln Gly
    130                 135                 140

Glu Cys Gly Ser Cys Trp Ala Phe Ala Thr Thr Ser Thr Ile Glu Gly
145                 150                 155                 160

Gln Trp Ala Leu Lys Thr Gly Gln Leu Val Asn Ala Ser Ala Gln Gln
                165                 170                 175

Leu Ile Asp Cys Ser Trp Ser Asn Gly Asn Glu Gly Cys Gly Gly Gly
            180                 185                 190

Asn Met Leu Gly Ala Tyr Thr Tyr Leu Ala Asp Glu Pro Phe Val Asp
        195                 200                 205

Ala Thr Asp Tyr Pro Tyr Leu Thr Lys Asp Tyr Val Cys Leu Asp Gln
    210                 215                 220

Gln Ile Lys Leu Lys Tyr Gly Lys Ile Arg Thr Ile Gly Phe Val Thr
225                 230                 235                 240

Pro Leu Asp Glu Thr Glu Leu Ala Leu Ala Val Lys Glu Ile Gly Pro
                245                 250                 255

Ile Ala Val Ala Ile Asp Gly Ser Ser Pro Tyr Leu Thr Phe Tyr Trp
            260                 265                 270

Glu Gly Ile Tyr Asp Asp Asp Thr Cys Thr Asn Gln Val Asn His Ala
        275                 280                 285
```

```
Val Thr Leu Val Gly Phe Gly Thr Asp Ser Asn Gly Ile Asp Tyr Trp
        290             295             300

Ile Val Lys Asn Ser Trp Gly Ala Asp Trp Gly Asp Asn Gly Tyr Phe
305             310             315             320

Lys Met Arg Arg Gly Val Asn Met Cys Gly Val Ala Glu Met Pro Met
            325             330             335

Tyr Ala Asn Phe
        340

<210> SEQ ID NO 11
<211> LENGTH: 255
<212> TYPE: PRT
<213> ORGANISM: Tetranychus urticae

<400> SEQUENCE: 11

Met Val Phe Lys Met Tyr Leu Asn Leu Ile Leu Ala Ile Thr Ala
1               5               10              15

Thr Asn Tyr Val Ser Thr Arg Ser Met Gly Ser Met Pro Gly Met Glu
            20              25              30

Leu Asp Val Asn Met Pro Met Asp Met Met Ser Asn Val Leu Gly Gly
        35              40              45

Ser Ala Phe Ala Gly Ser Asn Ala Asp Thr Glu Asn Gly Gly Ser Glu
    50              55              60

Ala Ala Ser Ser Ala Glu Ser Ala Ala Val Ala Asn Ala Glu Ala Thr
65              70              75              80

Thr Tyr Glu Glu Pro Asp Gly Glu Asp Asp Gly Leu Thr Tyr Gly Asn
            85              90              95

Asp Ile Ser Asp Ala Asp Ala Lys Thr Thr Ala Glu Ser Glu Ala Lys
        100             105             110

Ala Gly Ser Asp Asn Gly Ser Gly Asn Asn Gly Gly Asn Gly Tyr Asn
    115             120             125

Asn Asn Ser Asn Asn Gly Gly Ser Ser Ser Glu Thr Ser Ser Ser Ser
    130             135             140

Ala Ser Gly Ser Ser Asn Ser Glu Gly Ser Asp Asn Gly Ser Gly Asn
145             150             155             160

Asn Gly Val Asn Gly Tyr Asn Asn Asn Gly Asn Asn Gly Gly Ser Ser
            165             170             175

Ser Ala Thr Ser Ser Ser Ala Ala Ser Gly Ser Ser Asn Ser Glu Gly
        180             185             190

Ser Asp Asn Gly Ser Gly Asn Asn Gly Gly Asn Gly Tyr Asn Asn Asn
    195             200             205

Gly Asn Asn Gly Gly Ser Ser Ser Glu Thr Ser Ser Ser Ser Ala Ser
    210             215             220

Gly Ser Ser Asn Ser Glu Gly Ser Asp Asn Ser Ser Gly Asn Lys Gly
225             230             235             240

Gly Asn Gly Tyr Asn Asn Asn Gly Asn Asn Gly Gly Ser Ser Ser
            245             250             255

<210> SEQ ID NO 12
<211> LENGTH: 1311
<212> TYPE: PRT
<213> ORGANISM: Tetranychus urticae

<400> SEQUENCE: 12

Met Asn Phe Lys Met Cys Leu Ser Leu Phe Ile Phe Ala Leu Thr Ala
1               5               10              15

Thr Asn Tyr Val Ser Thr Arg Ile Ile Gly Met Pro Thr Asn Gly Leu
```

```
                20                  25                  30
Thr Asn Ser Met Ser Gly Ala Leu Ala Ser Ala Gly Ser Gln Ala Ser
            35                  40                  45

Asp Gly Ser Asp Asp Gly Thr Pro Ser Ile Glu Leu Ser Met Asp Gly
 50                  55                  60

Ile Gly Ser Met Pro Gly Thr Val Met Lys Ala Ile Leu Gly Asn Gln
 65                  70                  75                  80

Asp Asp Glu Asp Gly Asp Gln Glu Asp Glu Phe Asp Ser Ser Ser Ala
                85                  90                  95

Ser Ser Ser Ala Ala Ala Ala Ser Ser Ser Ser Glu Gly Glu Asp
            100                 105                 110

Asp Thr Asp Asn Glu Asn Gly Asp Glu Tyr Gly Pro Glu Asn Glu Ser
            115                 120                 125

Gly Asn Gly Tyr Gly Asn Glu Asn Asn Ser Glu Ser Gly Ala Asp Ser
            130                 135                 140

Gly Ser Gly Ala Gly Ala Gly Ser Gly Val Gly Ser Gly Ser Gly Ala
145                 150                 155                 160

Gly Ala Gly Ser Gly Ala Gly Ser Gly Ala Gly Ala Gly Ser
            165                 170                 175

Gly Ala Gly Asn Arg Asn Asp Ser Ser Arg Arg Ser Gly Ser Ser Ser
            180                 185                 190

Ser Thr Ser Ser Ser Ser Glu Gly Glu Asn Asn Asp Asn Asp
            195                 200                 205

Asn Asp Asn Glu Tyr Ser Ser Glu Asn Glu Asn Phe Asn Lys Tyr Ser
            210                 215                 220

Ser Gly Lys Glu Asn Gly Ser Ala Ser Gly Ala Ser Ala Gly Ser Gly
225                 230                 235                 240

Asn Gly Asn Gly His Ser Ser Asn Arg Glu Ser Ser Ser Ser Ser
            245                 250                 255

Ser Ser Ser Glu Asn Glu Asp Ser Ala Asp Asn Glu Asn Ser Asn Asn
            260                 265                 270

Tyr Ser Ser Gly Asn Lys Asn Asn Gly Ser Gly Ser Lys Ser Ser Ala
            275                 280                 285

Ser Ser Ala Glu Ser Ser Ala Ser Glu Asn Ser Asn Ser Tyr Gly Ser
            290                 295                 300

Ser Asn Ser Asp Asn Thr Gly Gly His Gly Ser Ala Gln Gly Ser Ser
305                 310                 315                 320

Ser Ser Ser Ala Ala Ser Ser Ser Ser Thr Lys Asp Asn Glu
            325                 330                 335

Asn Arg Asp Asn Val Ser Asp Asn Asp Tyr Asp Ser Ser Asn Gly Asn
            340                 345                 350

Gly Asn Gly Tyr Ser Asn Asn Asn Asp Ser Gly Ala Asn Ser Gln Glu
            355                 360                 365

Tyr Phe Ser Ile Phe Ser Gly Asn Gly Asn Gly Tyr Gly Asn Gly Asn
            370                 375                 380

Asn Gly Ser Gly Ser Gly Ser Gly Ser Gly Ser Gly Ser Gly
385                 390                 395                 400

Ala Gly Ser Gly Ser Gly Ser Ser Ala Gly Ser Gly Ser Gly Ser Gly
            405                 410                 415

Ser Gly Ser Gly Ser Gly Ser Gly Ala Gly Ser Gly Ser Gly
            420                 425                 430

Ser Ser Ala Gly Ser Gly Ser Ser Ala Ala Ser Ser Gly Ser Ser
            435                 440                 445
```

-continued

Gly Ser Ser Ser Gly Ser Gly Asn Gly Tyr Gly Ser Gly Asn Gly Asn
                450                 455                 460
Gly Tyr Gly Asn Gly Asn Asn Gly Ser Gly Ser Gly Ser Gly
465             470             475             480
Ser Gly Ser Gly Ser Gly Ser Gly Ala Gly Ser Gly Ser Ser Ala
                485                 490                 495
Ala Ser Ser Gly Ser Ser Gly Ser Ser Ser Gly Ser Gly Asn Gly Tyr
            500                 505                 510
Gly Ser Gly Asn Gly Asn Gly Tyr Gly Asn Gly Asn Asn Gly Ser Gly
            515                 520                 525
Ser Gly Ser Gly Ser Gly Ser Gly Ser Gly Ser Gly Ser Gly
            530                 535                 540
Ser Gly Ser Gly Ser Gly Ser Gly Ala Gly Ser Gly Ser Asn Ala Gly
545                 550                 555                 560
Ser Gly Ser Gly Ala Gly Ser Gly Ser Ser Ala Ala Ser Ser Gly
                565                 570                 575
Ser Ser Ala Ser Ser Gly Ser Gly Asn Gly Tyr Gly Ser Gly Asn
            580                 585                 590
Gly Asn Gly Tyr Gly Asn Gly Asn Asn Gly Ser Gly Ser Gly Ser Gly
            595                 600                 605
Ser Gly Ser Gly Ser Gly Ser Gly Ser Gly Ser Ser Ala Ala Ser
            610                 615                 620
Ser Gly Ser Gly Ala Gly Ser Val Ser Asn Gly Tyr Gly Ser Gly Ser
625                 630                 635                 640
Gly Ser Thr Ser Gly Ser Arg Ile Cys Ser Leu Phe Arg Phe Ser Ile
                645                 650                 655
Gln Val His Val Ser Val Asp Thr Val Met Val Gln Glu Lys Ala Met
            660                 665                 670
Ala Ser Glu Met Val Ile Met Asp Leu Ala Leu Asp Ala Ala Ser Ser
            675                 680                 685
Gly Ser Gly Leu Thr Ser Gly Ser Gly Ser Gly Ser Gly Ser Gly Pro
            690                 695                 700
Gly Ser Gly Ser Gly Ser Gly Ser Gly Ser Gly Ser Gly Ser Gly Ser
705                 710                 715                 720
Gly Ser Gly Ser Gly Ser Gly Ser Gly Ser Gly Ser Gly Ser Gly Ser
                725                 730                 735
Gly Ser Gly Ser Gly Ser Gly Ser Ser Ala Gly Ser Gly Ser Ser Ser
            740                 745                 750
Ala Ala Ser Ser Gly Ser Ser Gly Ser Ser Gly Ser Gly Asn Gly
            755                 760                 765
Tyr Gly Ser Gly Asn Gly Asn Gly Tyr Gly Asn Gly Asn Asn Gly Ser
770                 775                 780
Gly Ser Gly Ser Gly Ser Gly Ser Gly Ser Gly Ser Gly Ser Gly Ala
785                 790                 795                 800
Gly Ser Gly Ser Ser Ser Ala Ala Ser Ser Gly Ser Ser Gly Ser Ser
                805                 810                 815
Ser Gly Ser Gly Asn Gly Tyr Gly Ser Gly Asn Asp Asn Val Tyr Gly
            820                 825                 830
Asn Gly Asn Asn Gly Ser Gly Ser Gly Ala Gly Ser Gly Ser
            835                 840                 845
Gly Ala Gly Ser Gly Ser Ser Ser Ala Ala Ser Ser Gly Ser Ser Gly
            850                 855                 860
Ser Ser Ser Gly Ser Glu Asn Gly Tyr Gly Ser Gly Asn Gly Asn Gly
865                 870                 875                 880

```
Tyr Gly Asn Gly Asn Asn Gly Ser Gly Ser Gly Ser Gly Ala
            885                 890                 895
Gly Ser Gly Ser Gly Ser Ser Ala Ala Ser Ser Gly Ser Ser Ala
900                 905                 910
Ser Ser Ser Gly Ser Gly Asn Gly Tyr Gly Ser Gly Asn Gly Asn Gly
            915                 920                 925
Tyr Gly Asn Gly Asn Asn Gly Ser Gly Ser Gly Ser Gly Ser
            930                 935                 940
Gly Ser Gly Ser Gly Ser Gly Ala Gly Ser Gly Ser Asn Ala Gly Ser
945                 950                 955                 960
Gly Ser Gly Ala Gly Ser Gly Ser Ser Ala Ala Ser Gly Ser Ser
                965                 970                 975
Ala Ser Ser Ser Gly Ser Gly Asn Gly Tyr Ser Gly Asn Gly Asn
            980                 985                 990
Gly Tyr Gly Asn Gly Asn Asn Val  Ser Gly Ser Gly Ser  Gly Ser Gly
            995                 1000                1005
Ser Gly  Ser Gly Ala Ser Ser  Gly Ser Ser Ser Ala  Ala Ser Ser
1010                 1015                1020
Gly Ser  Ser Gly Ser Gly Asn  Gly Tyr Gly Ser Gly  Ser Gly Ser
1025                 1030                1035
Gly Ser  Gly Ser Gly Ser Gly  Ser Gly Ser Gly Thr  Ser Ser Gly
1040                 1045                1050
Ser Gly  Ser Gly Ser Asn Ala  Gly Ser Gly Ser Gly  Ala Gly Ser
1055                 1060                1065
Gly Ser  Ser Ser Ala Ala Ser  Ser Gly Ser Ser Gly  Ser Gly Asn
1070                 1075                1080
Gly Tyr  Gly Ser Gly Ser Gly  Ser Gly Ser Gly Thr  Ser Ser Gly
1085                 1090                1095
Ser Gly  Ser Gly Ser Asn Ala  Gly Ser Gly Ser Gly  Ala Gly Ser
1100                 1105                1110
Gly Ser  Ser Ser Ala Thr Ser  Ser Gly Ser Ser Gly  Arg Gly Asn
1115                 1120                1125
Gly Tyr  Gly Ser Gly Ser Gly  Ser Gly Ser Gly Ser  Gly Ser Gly
1130                 1135                1140
Ser Gly  Ser Gly Ser Gly Ser  Gly Ser Gly Ser Gly  Ser Gly Ser
1145                 1150                1155
Gly Ala  Gly Ser Gly Ala Gly  Ser Gly Ala Gly Ser  Gly Ala Ser
1160                 1165                1170
Ala Gly  Ser Gly Ser Gly Ser  Gly Ala Gly Ser Gly  Ala Asn Ser
1175                 1180                1185
Gly Ser  Gly Ser Gly Ser Gly  Ser Gly Asn Gly Lys  Gly Asn Gly
1190                 1195                1200
His Gly  Lys His Gly Ser Gly  Ser Asp Ser Ala Ser  Gly Ala Ala
1205                 1210                1215
Ala Ser  Ala Glu Ser Ser Ser  Gly Ser Gly Ser Ser  Ala Arg Lys
1220                 1225                1230
Val Gly  Ser Ala Ser Ser Ser  Gly Ser Ser Ala Ser  Gly Asn Asn
1235                 1240                1245
Ser Arg  Pro Gly Ser Gly Ser  Arg Pro Ile Thr Asn  Lys Gln Ser
1250                 1255                1260
Arg Ser  Gly Met Gln Ser Gly  Phe Gly Ser Ala Lys  Ala Ser Ala
1265                 1270                1275
Ser Ser  Val Leu Arg Ser Asn  Pro Val Asn Lys Ala  Ser Lys Thr
```

-continued

```
                1280                1285                1290
Ser Gly Asn Leu Ile Ser Phe Glu Met Pro Gly Phe Asp Leu Ser
        1295                1300                1305

Met Gly Arg
        1310

<210> SEQ ID NO 13
<211> LENGTH: 359
<212> TYPE: PRT
<213> ORGANISM: Tetranychus urticae

<400> SEQUENCE: 13

Ser Ser Ala Ala Ala Ala Ser Gly Ala Ser Ser Asn Gly Ser Asp Asn
1               5                   10                  15

Asn Gly Gly Asn Asn Val Asn Asn Gly Ser Ser Ser Ala Ala Ala
            20                  25                  30

Ser Ser Ala Ala Ala Ala Ser Gly Ala Ser Ser Asn Gly Ser Asp Asn
        35                  40                  45

Asn Gly Gly Asn Asn Gly Asn Asn Gly Ser Ser Ser Ala Ala Ala
        50                  55                  60

Ser Ser Ala Ala Ala Ala Ser Gly Ala Ser Ser Asn Gly Ser Asp Asn
65                  70                  75                  80

Asn Gly Gly Asn Asn Gly Asn Asn Gly Ser Ser Ser Ala Ala Ala
                85                  90                  95

Ser Ser Ala Ala Ala Ala Ser Gly Ala Ser Ser Asn Gly Ser Asp Asn
                100                 105                 110

Asn Gly Gly Asn Asn Val Asn Asn Gly Ser Ser Ser Ala Ala Ala
            115                 120                 125

Ser Ser Ala Ala Ala Ala Ser Gly Ala Ser Ser Asn Gly Ser Asp Asn
        130                 135                 140

Asn Gly Gly Asn Asn Gly Asn Asn Gly Ser Ser Ser Ala Ala Glu
145                 150                 155                 160

Ser Ser Ala Ala Ala Ala Ser Gly Ala Ser Ser Asn Gly Ser Asp Asn
                165                 170                 175

Asn Gly Gly Asn Asn Gly Asn Asn Gly Ser Ser Ser Ala Ala Ala
            180                 185                 190

Ser Ser Ala Ala Ala Ala Ser Gly Ala Ser Ser Asn Gly Ser Ser Lys
            195                 200                 205

Asn Ala Gly Asn Ser Gly Asn Asn Gly Ala Ser Ser Ala Ala Gly
        210                 215                 220

Ser Ala Ser Asn Gly Ser Asn Lys Asn Gly Asn Ala Gly Asn Asn Ser
225                 230                 235                 240

Gly Ala Ser Ser Ala Ala Gly Ser Ser Asn Gly Ser Gly Gln Lys Val
                245                 250                 255

Asn Asn Ser Gly Ser Ser Thr Thr Ala Gly Ser Gly Asn Asn Gly Gly
            260                 265                 270

Asn Gly Gln Lys Ser Gly Gln Ala Val Ser Gly Ser Ala Ala Ser
        275                 280                 285

Ser Ala Ala Ala Ala Ser Ala Gly Asn Gly Asn Ala Lys Lys Gly Gly
        290                 295                 300

Lys Gln Gly Asn Gly Lys Gly Asn Ala Ala Ala Ala Ala Ala Ala
305                 310                 315                 320

Ala Ser Ser Ser Ser Gly Asn Gly Ser Lys Ser Gly Lys Asn Pro Ser
            325                 330                 335

Lys Gln Gly Ile Ile Pro Ala Met Met Ser Lys Ile Pro Val Thr Met
```

Pro Leu Thr Val Ser Leu Phe
            355

<210> SEQ ID NO 14
<211> LENGTH: 685
<212> TYPE: PRT
<213> ORGANISM: Tetranychus urticae

<400> SEQUENCE: 14

Met Val Phe Lys Met Tyr Leu Asn Leu Leu Ile Leu Ala Ile Thr Ala
1               5                   10                  15

Thr Ser Tyr Val Ser Thr Arg Ser Ile Ser Pro Met Glu Asp Met Glu
            20                  25                  30

Val Asp Val Asn Met Pro Met Gly Met Ile Ser Asn Val Met Ser Gly
        35                  40                  45

Ser Asn Ala Phe Ala Gly Ser Asn Ala Ile Thr Glu Thr Gly Gly Ser
    50                  55                  60

Asp Gly Asn Ser Gly Ala Ala Ser Ala Ala Ser Ala Ala Ala Gly Ala
65                  70                  75                  80

Thr Thr Asn Asp Gly Ser Asn Gly Asp Asn Glu Asn Asp Gly Asp Asp
                85                  90                  95

Gly Gly Leu Gly Tyr Glu Asn Asn Glu Ser Thr Ala Glu Thr Thr Ala
            100                 105                 110

Asp Ala Ser Ala Gly Asn Ala Asn Asn Ala Asn Ala Glu Asn Ser Gln
        115                 120                 125

Asn Val Ala Asn Glu Ser Gln Ala Glu Thr Gly Asn Gln Ala Asp Asn
    130                 135                 140

Asn Glu Gly Ser Val Asp Asn Gly Ser Asn Glu Arg Ser Asn Ala Ala
145                 150                 155                 160

Thr Gly Ser Ser Ser Asp Gly Glu Asn Asn Gly Gly Asn Asp Tyr
                165                 170                 175

Gly Lys Asn Asp Asn Gly Ser Gly Ser Arg Ala Ala Thr Ser Ser Ser
            180                 185                 190

Ala Ala Ser Lys Gly Gly Ser Ser Asn Gly Ser Asp Asn Asn Gly Gly
        195                 200                 205

Asn Asn Gly Ser Gly Ser Ser Ala Ala Ala Ser Ser Ser Ala Ala Ser
    210                 215                 220

Ser Ala Gly Ser Ser Ser Ser Glu Gly Thr Asp Asn Gly Ser Asp Asn
225                 230                 235                 240

Asn Glu Gly Asn Asn Gly Ser Gly Ser Ser Ala Ala Ala Ser Ser Ser
                245                 250                 255

Ala Ala Ser Ser Ala Gly Ser Ser Ser Glu Ala Ser Asp Asn Gly
            260                 265                 270

Ser Asp Asn Asn Gly Gly Asn Asn Gly Ser Gly Ser Ser Ala Ala Ala
        275                 280                 285

Ser Ser Ser Ala Ala Ser Ser Ala Gly Ser Ser Ser Ser Glu Gly Thr
    290                 295                 300

Asp Asn Gly Ser Asp Asn Asn Gly Gly Asn Asn Gly Ser Gly Ser Ser
305                 310                 315                 320

Ala Ala Ala Ser Ser Ala Ala Ser Ser Ala Gly Ser Ser Ser Ser
                325                 330                 335

Glu Ala Ser Asp Asn Gly Ser Asp Asn Asn Gly Gly Asn Asn Gly Ser
            340                 345                 350

Gly Ser Ser Ala Ala Ala Ser Ser Ser Ala Ala Ser Ser Ala Gly Ser

```
                    355                 360                 365
Ser Asn Gly Ser Asp Asn Asn Gly Gly Asn Asn Gly Ser Gly Ser Ser
            370                 375                 380

Ala Ala Ala Ser Ser Ala Ala Ser Ser Ala Gly Ser Ser Ser Ser
385                 390                 395                 400

Glu Gly Ser Asp Asn Gly Ser Asp Asn Asn Asn Gly Asn Asn Gly Ser
                405                 410                 415

Ser Ser Ser Ala Ala Ser Ser Ala Ala Ala Ser Gly Ala Ser Ser
            420                 425                 430

Asn Gly Ser Asp Asn Asn Gly Gly Asn Asn Gly Asn Asn Gly Ser Ser
                435                 440                 445

Ser Ser Ala Ala Ser Ser Ala Ala Ala Ser Gly Ala Ser Ser Asn
            450                 455                 460

Gly Ser Asp Asn Asn Gly Gly Asn Asn Gly Asn Asn Gly Ser Ser Ser
465                 470                 475                 480

Ser Ala Ala Ser Ser Ala Ala Ala Ser Gly Ala Ser Ser Asn Gly
                485                 490                 495

Ser Asp Asn Asn Gly Gly Asn Asn Gly Asn Asn Gly Ser Ser Ser Ser
            500                 505                 510

Ala Ala Ser Ser Ala Ala Ala Ser Gly Ala Ser Ser Asn Gly Ser
515                 520                 525

Asp Asn Asn Gly Gly Asn Asn Gly Asn Gly Ser Gly Ser Ser Ala Ala
            530                 535                 540

Thr Ser Ala Ala Ala Ala Thr Ser Gly Ala Ser Ser Asn Gly Ser Asn
545                 550                 555                 560

Asn Asn Gly Gly Asn Asn Gly Asn Asn Ala Ser Ser Ser Ala Ala
                565                 570                 575

Ser Gly Gly Thr Ser Asn Gly Ser Gly Asn Lys Val Asn Asn Thr Gly
            580                 585                 590

Ser Ser Ala Gly Ser Ala Thr Gly Ser Asn Lys Asn Lys Gly Asn Gly
            595                 600                 605

Gln Asn Asn His Gly Ser Ala Ser Ser Ser Gly Ala Ala Thr Gly Gly
            610                 615                 620

Ala Gly Asn Gly Asn Ala Lys Lys Ser Gly Lys Gln Gly Asn Ser Gln
625                 630                 635                 640

Gly Asn Ser Ala Ala Ala Ser Ala Ala Ala Ser Ser Ala Ser Gly Asn
                645                 650                 655

Gly Ser Lys Pro Gly Lys Ser Pro Val Lys Gln Gly Ile Ile Pro Ala
            660                 665                 670

Met Met Ser Lys Ile Pro Met Lys Val Ser Leu Met Phe
            675                 680                 685

<210> SEQ ID NO 15
<211> LENGTH: 239
<212> TYPE: PRT
<213> ORGANISM: Tetranychus urticae

<400> SEQUENCE: 15

Ala Ser Gly Ser Ser Ala Ser Asn Gly Ser Asp Asn Asn Gly Gly Asn
1               5                   10                  15

Asn Gly Asn Asn Gly Ser Ser Ser Ala Ala Ala Ser Ser Ala Ala Ala
                20                  25                  30

Ala Ser Gly Ser Ser Ala Ser Asn Gly Ser Asp Asn Asn Gly Gly Asn
            35                  40                  45

Asn Gly Asn Asn Gly Ser Ser Ser Ala Ala Ala Ser Ser Ala Ala Ala
```

```
            50                  55                  60
Ala Ser Gly Ser Ser Ala Ser Asn Gly Ser Asp Asn Gly Gly Asn
 65                  70                  75                  80

Asn Gly Asn Asn Gly Ser Ser Ala Ala Ala Ser Ser Ala Ala Ala
                     85                  90                  95

Ser Ser Gly Ala Asn Ala Asn Asn Asn Gly Ser Asn Asn Gly Asn
                    100                 105                 110

Asn Ser Gly Ser Ser Ala Ala Val Thr Ser Ser Asn Gly Ser Gly
                    115                 120                 125

Gln Lys Val Asn Asn Ala Gly Ser Ser Gly Ala Thr Ala Gly Ser
                    130                 135                 140

Gly Ser Asn Gly Gly Asn Arg Gln Asn Asn Gly Gly Ser Lys Gly Ala
145                 150                 155                 160

Asn Gly Ser Ala Ala Ser Ser Ala Ser Ser Ser Ala Ala Ser Ser Gly
                    165                 170                 175

Ser Ala Gly Asn Gly Asn Ser Lys Arg Gly Gly Lys Gln Gly Asn Gly
                    180                 185                 190

Gln Gly Asn Ala Gly Ala Ala Thr Ser Ala Ala Ala Ser Ser Ala Ser
                    195                 200                 205

Gly Lys Gly Ser Lys Ser Gly Lys Ser Pro Ala Lys Gln Gly Ile Ile
210                 215                 220

Pro Ala Met Met Ser Lys Ile Pro Ala Leu Ser Val Ser Met Phe
225                 230                 235
```

<210> SEQ ID NO 16
<211> LENGTH: 450
<212> TYPE: PRT
<213> ORGANISM: Tetranychus urticae

<400> SEQUENCE: 16

```
Met Val Phe Lys Met Tyr Leu Asn Leu Leu Ile Leu Ala Ile Thr Ala
  1               5                  10                  15

Thr Asn Tyr Val Ser Thr Arg Ser Met Gly Ser Met Pro Gly Met Glu
                 20                  25                  30

Leu Asp Val Asn Met Pro Met Asp Met Met Ser Asn Val Leu Gly Gly
                 35                  40                  45

Ser Ala Phe Ala Gly Ser Asn Ala Asp Thr Glu Asn Gly Gly Ser Glu
 50                  55                  60

Ala Ala Ser Ser Ala Glu Ser Ala Ala Val Ala Asn Ala Glu Ala Thr
 65                  70                  75                  80

Thr Tyr Glu Glu Pro Asp Gly Glu Asp Asp Gly Leu Thr Tyr Gly Asn
                 85                  90                  95

Asp Ile Ser Asp Ala Asp Ala Lys Thr Thr Ala Glu Ser Glu Ala Lys
                100                 105                 110

Ala Gly Ser Asp Asn Gly Ser Gly Asn Asn Gly Asn Gly Tyr Asn
                115                 120                 125

Asn Asn Ser Asn Asn Gly Gly Ser Ser Ser Glu Thr Ser Ser Ser Ser
130                 135                 140

Ala Ser Gly Ser Ser Asn Ser Glu Gly Ser Asp Asn Gly Ser Gly Asn
145                 150                 155                 160

Asn Gly Val Asn Gly Tyr Asn Asn Gly Asn Gly Ser Ser
                165                 170                 175

Ser Ala Thr Ser Ser Ser Ala Ala Ser Gly Ser Ser Asn Ser Glu Gly
                180                 185                 190

Ser Asp Asn Gly Ser Gly Asn Asn Gly Gly Asn Gly Tyr Asn Asn Asn
```

```
                   195                 200                 205
Gly Asn Asn Gly Gly Ser Ser Ser Glu Thr Ser Ser Ser Ala Ser
210                 215                 220

Gly Ser Ser Asn Ser Glu Gly Ser Asp Asn Ser Ser Gly Asn Lys Gly
225                 230                 235                 240

Gly Asn Gly Tyr Asn Asn Gly Asn Asn Gly Gly Ser Ser Ser Ala
            245                 250                 255

Thr Ser Ser Ser Ala Ser Gly Ser Ser Asn Ser Glu Gly Ser Asp
                260                 265                 270

Asn Gly Ser Gly Asn Asn Gly Gly Asn Gly Tyr Asn Asn Gly Asn
            275                 280                 285

Asn Gly Gly Ser Arg Ser Ser Ser Glu Thr Ser Ser Ser Ala Ser
290                 295                 300

Gly Ser Ser Asn Ser Glu Gly Ser Asp Asn Ser Ser Gly Asn Lys Gly
305                 310                 315                 320

Gly Asn Gly Tyr Asn Asn Gly Asn Asn Gly Gly Ser Ser Ser Ala
            325                 330                 335

Thr Ser Ser Ser Ala Ser Gly Ser Ser Asn Ser Glu Gly Ser Asp
                340                 345                 350

Asn Gly Ser Gly Asn Asn Gly Gly Asn Gly Tyr Asn Asn Gly Asn
            355                 360                 365

Asn Gly Gly Ser Ser Ser Ala Thr Ser Ser Ser Ala Ala Ser Gly Ser
370                 375                 380

Ser Thr Ser Asn Gly Ser Asp Asn Asn Gly Gly Asn Asn Gly Asn Asn
385                 390                 395                 400

Gly Ser Ser Ser Ala Ala Ala Ala Ser Gly Ser Ser Ala Ser Asn Gly
                405                 410                 415

Ser Asp Asn Asn Gly Gly Asn Asn Gly Asn Asn Gly Ser Ser Ser Ala
            420                 425                 430

Ala Ala Thr Ser Ser Ser Ser Ala Ser Gly Ser Ser Thr Ser Asp Gly
                435                 440                 445

Ser Ala
    450

<210> SEQ ID NO 17
<211> LENGTH: 900
<212> TYPE: PRT
<213> ORGANISM: Tetranychus urticae

<400> SEQUENCE: 17

Met Val Leu Lys Ile Tyr Leu Ser Leu Leu Ile Leu Val Ile Thr Ala
1               5                   10                  15

Asn Asn Tyr Val Ser Thr Arg Ser Ile Val Asp Pro Asp Ala Ile Leu
            20                  25                  30

Ser Asn Met Pro Ser Met Glu Phe Ser Ile Ser Asp Ala Ala Ala Thr
        35                  40                  45

Ala Thr Ser Ser Ala Glu Asp Lys Ser Ser Leu Met Asp Ile Thr Ile
    50                  55                  60

Gly Gly Glu Asp Asn Asp Asn Asp Ser Asn Gly Asp Gly Gly Ser
65                  70                  75                  80

Ser Ala Asn Ala Gln Ala Glu Ser Ala Ala Asp Ser Ala Thr Gly Ala
                85                  90                  95

Thr Asn Gly Asn Gly Asn Ser Gly Ser Asn Gly Ala Gly Asn Gly Ser
            100                 105                 110

Ser Ala Asn Ala Gln Ala Glu Ser Ala Ala Asp Ser Ala Thr Gly Ala
```

```
                    115                 120                 125
Thr Asn Gly Asn Gly Asn Ser Gly Ser Asn Gly Ala Asp Asn Gly Ser
130                 135                 140

Ser Ala Asn Ala Gln Ala Glu Ser Ala Ala Asp Ser Ala Thr Gly Ala
145                 150                 155                 160

Thr Asn Gly Asn Gly Asn Ser Gly Ser Asn Gly Ala Asp Asn Gly Ser
                    165                 170                 175

Ser Ala Asn Ala Gln Ala Glu Ser Ala Ala Asp Ser Ala Thr Gly Gly
                    180                 185                 190

Ser Ser Ser Thr Ser Glu Gly Ser Ser Gly Gly Asn Asp Asn Gly
        195                 200                 205

Gly Asn Ser Gly Lys Asn Ser Gly Ser Gly Ser Asp Ser Asn Ala Asn
        210                 215                 220

Ala Asn Ser Gln Gly Asp Ser Ser Asp Asn Gly Asn Gly Lys Asn
225                 230                 235                 240

Gly Gly Asn Arg Gly Asn Asn Gly Ser Asn Ala Asn Ala Gln Ala Asp
                    245                 250                 255

Ser Ser Ala Asp Ser Thr Ser Gly Gly Ser Asp Ser Gly Ser His Ser
                260                 265                 270

Asp Ser Gly Ser Gly Ser Gly Ser Gly Ser Gly Ser Gly Ser Gly Ser
        275                 280                 285

Gly Ser Gly Ser Gly Ser Gly Ser Gly Ser Gly Ser Gly Ser Asp Ser
290                 295                 300

Gly Ser Gly Ser Gly Ser Gly Ser Gly Gly Ser Ser Glu Gly Gly
305                 310                 315                 320

Asn Asn Gly Asp Asn Thr Gly Asp Ser Asn Ala Ala Ala Ser Ala Ala
                    325                 330                 335

Ala Ala Ala Ala Ala Ala Ala Gly Asn Ser Asn Gly Ala Gly Asp Ser
            340                 345                 350

Thr Gly Asn Ala Leu Gly Leu Ala Ser Ser Ala Ala Ala Ala Ala Ser
        355                 360                 365

Ser Ala Ala Ser Lys Ala Lys Asn Leu Leu Phe Gly Thr Asp Thr Asp
370                 375                 380

Ser Phe Ala Ser Ala Ser Ser Leu Ala Asp Ala Val Ser Ser Ser Asp
385                 390                 395                 400

Ala Asp Asn Gly Asp Asn Asn Thr Asn Asp Asn Gly Ala Asn Lys Ser
                    405                 410                 415

Asn Gly Ser Gly Ser Ser Ser Ser Ser Ala Ser Ser Ser Ser
            420                 425                 430

Ser Gly Gly Asn Gly Asn Ser Gly Asn Ser Gly Asn Gly Ser Gly Ser
            435                 440                 445

Gly Ser Gly Ser Gly Ser Gly Ala Gly Ser Gly Ser Gly Ser Gly Ser
        450                 455                 460

Gly Ser Gly Ser Gly Ser Gly Ser Ala Ser Ser Glu Glu Asn Gly
465                 470                 475                 480

Asn Gly Asn Ser Asn Gly Asn Ala Gly Ser Asn Ala Glu Ala Glu Ala
            485                 490                 495

Asn Ser Tyr Thr Ser Gly Glu Asn Asn Asn Glu Ala Asp Lys Ser Asn
        500                 505                 510

Gly Ser Ser Ser Ser Ser Ser Ser Ser Ser Ser Ser Ser Gly Gly
        515                 520                 525

Arg Gly Asn Gly Gly Asn Ser Gly Asn Gly Ser Gly Ser Gly Ser Gly
530                 535                 540
```

Ser Gly Ser Gly Ser Gly Ser Gly Ser Gly Ser Gly Ser Gly Ser Gly
545                 550                 555                 560

Ser Gly Ser Gly Ser Gly Ser Gly Ser Gly Ser Gly Ser Gly Ser Gly
            565                 570                 575

Ser Gly Ser Gly Ser Gly Gly Ser Ser Glu Gly Gly Asn Asn Gly
        580                 585                 590

Asp Asn Thr Gly Asn Ser Asn Gly Ala Gly Asp Ser Thr Gly Asn Ala
            595                 600                 605

Leu Gly Leu Ala Ser Ser Ala Ala Ala Ala Ser Ser Ala Ala Ser
        610                 615                 620

Lys Ala Lys Asn Leu Leu Phe Gly Thr Asp Thr Asp Ser Phe Ala Ser
625                 630                 635                 640

Ala Ser Ser Leu Ala Asp Ala Val Ser Ser Asp Ala Asp Asn Gly
            645                 650                 655

Asp Asn Asn Thr Asn Asp Asn Gly Ala Asn Lys Ser Asn Gly Ser Gly
            660                 665                 670

Ser Ser Ser Ser Ser Ser Ala Ser Ser Ser Ser Ser Gly Gly Asn
        675                 680                 685

Gly Asn Ser Gly Asn Ser Gly Asn Gly Ser Gly Ser Gly Ser Gly Ser
690                 695                 700

Gly Ser Gly Ser Gly Ser Gly Ser Gly Ser Gly Ser Gly Ser Gly Ser
705                 710                 715                 720

Gly Ser Gly Ser Gly Ser Gly Ser Gly Ser Gly Ser Gly Ser Gly Ser
            725                 730                 735

Gly Ser Asp Ser Gly Ser Gly Gly Ser Ser Ser Thr Gly Arg
        740                 745                 750

Ser Val Asn Asn Lys Ser Ser Gly Gly Asn Asn Ala Ala Ala Lys Ser
            755                 760                 765

Ala Ala Ser Ala Thr Ser Gly Asn Gly Thr Gly Asn Asn Lys Gln Asn
        770                 775                 780

Gly Gly Asn Asn Ala Ser Gly Ser Ser Ser Ser Ala Ser Ser Ser Ser
785                 790                 795                 800

Gly Gly Ser Ser Ser Ser Gly Gly Asn Gly Ser Gly Lys Asn Lys Pro
            805                 810                 815

Ser Gly Gly Asn Asn Ala Val Ser Lys Ser Ala Ala Ser Ser Ser Ser
            820                 825                 830

Arg Asn Gly Ser Gly Asn Lys Lys Ala Asn Arg Pro Gly Ser Gly Ser
        835                 840                 845

Ser Ser Ser Ala Asp Ala Ala Ala Ser Ser Ser Phe Gly Lys
        850                 855                 860

Gly Lys Asn Ser Ile Pro Lys Ser Gly Lys Gly Pro Val Lys Pro Ala
865                 870                 875                 880

Leu Pro Ile Asn Pro Ala Asn Met Leu Ser Gly Leu Pro Val Asn Leu
            885                 890                 895

Gln Ile Asn Ile
        900

<210> SEQ ID NO 18
<211> LENGTH: 1672
<212> TYPE: PRT
<213> ORGANISM: Tetranychus urticae

<400> SEQUENCE: 18

Met Thr Ile Pro Pro Leu Asp His Gln Ser Ser Ala Glu Ser Gly
1               5                   10                  15

```
Ser Ile Arg Asn Ser Asp Ser Asp Ser Gln Ser Tyr Ser Pro Val Thr
            20                  25                  30

Gln Gln Ser Gly Glu Val Ser Ile Asp Val Thr Val Gly Ser Val Asp
        35                  40                  45

Pro Val Ser Thr Glu Ser Ser Gln Ala Thr Gln Thr Ser Ser Gln
    50                  55                  60

Ser Phe Ser Asn Val Ser Ile Ser Val Ala Ala Ser Ser Glu Gly Val
65                  70                  75                  80

Ala Pro Thr Thr Gln Ala Thr Ser Ser Thr Pro Asp Gly Asn Thr Val
                85                  90                  95

Val Val Ile Ile Ala Ser Asn Asp Asn Asp Ser Val Ser Ser Gly Thr
            100                 105                 110

Ser Ser Gln Ser Ser Ser Tyr Ala Thr Asn Ser Gln Ile Ser Gln Ala
            115                 120                 125

Ser Asn Ser Thr Val Thr Pro Leu Asn Glu Asp Leu Gly Pro Ala Phe
    130                 135                 140

Thr Thr Ser Ser Glu Ser Leu Ser Asp Glu Ile Ala Phe Glu Phe Ser
145                 150                 155                 160

Thr Asp Ser Tyr Ile Asp Ala Thr Val Gly Ser Ser Ala Ser Ser Ala
                165                 170                 175

Thr Ser Asn Ile Ser Ile Ser Val Ser Thr Ser Ser Glu Gly Asn Glu
            180                 185                 190

Pro Thr Thr Gln Ala Thr Ser Ser Thr Ser Asp Gly Asn Thr Val Val
    195                 200                 205

Val Ile Val Thr Thr Asn Asp Asn Asp Ser Ala Ser Ser Gly Thr Pro
    210                 215                 220

Ser Gln Thr Ser Asn Gln Gln Thr Ser Ser Ser Ser Ser Ala Thr
225                 230                 235                 240

Ile Asn Gln Val Ser Gln Glu Ser Asn Ser Thr Val Asp Pro Ile Ser
                245                 250                 255

Glu Val Gln Ser Thr Gln Ser Ser Ser Ser Ser Tyr Ala Asp Thr
                260                 265                 270

Thr Val Gly Ser Ser Glu Val Val Asn Gln Ser Thr Pro Gln Thr Ser
        275                 280                 285

Ser Gln Ser Ser Thr Pro Ser Ser Ser Ala Glu Ser Asp Ser Ile Arg
    290                 295                 300

Val Ser Asp Gln Glu Ser Tyr Asn Ala Val Thr Gln Gln Ser Gly Glu
305                 310                 315                 320

Ile Ser Val Asp Val Thr Val Gly Ser Ile Val Pro Val Ser Thr Glu
                325                 330                 335

Thr Ser Ser Gln Ala Thr Gln Ser Thr Ser Gln Ser Ser Ser Asn Val
            340                 345                 350

Ser Val Ser Val Ser Thr Glu Asp Asp Glu Pro Thr Thr Ser Ser Pro
        355                 360                 365

Ser Asp Gly Asn Thr Val Val Val Ile Val Thr Thr Asn Glu Ser Asp
    370                 375                 380

Ser Ala Ser Ser Gly Thr Pro Ser Gln Ser Ala Asn Gln Gln Thr Ser
385                 390                 395                 400

Ser Ser Ser Ser Ser Val Thr Asn Asn Gln Ala Ser Gln Glu Asn Arg
                405                 410                 415

Pro Thr Val Ala Ser Leu Tyr Val Asp Ser Thr Val Gly Ser Ala Val
            420                 425                 430

Thr Glu Asn Gln Ser Val Ser Gln Thr Ser Thr Ser Ser Leu Glu Tyr
        435                 440                 445
```

```
Ser Thr Gln Ala Ser Ser Gln Glu Ser Gly Glu Ile Arg Thr Ser Asp
    450                 455                 460

Ser Glu Ser Ser Asn Pro Val Ser Gln Gln Ser Ser Glu Val Ser Ile
465                 470                 475                 480

Asp Val Thr Val Gly Ser Val Asp Ser Val Ala Thr Glu Thr Ser Ser
                485                 490                 495

Gln Ala Ser Gln Thr Pro Ser Gln Ser Ser Asn Val Ser Val Ser
        500                 505                 510

Val Pro Ile Thr Ser Glu Gly Asn Glu Pro Thr Thr Ser Asn Thr Ser
            515                 520                 525

Asp Gly Asn Thr Val Val Ile Val Thr Thr Asn Asn Asp Ser Gly
        530                 535                 540

Ser Ala Val Thr Ser Ser Gln Ser Ser Asn Gln Asn Val Pro Ser
545                 550                 555                 560

Leu Asn Glu His Pro Thr Glu Ser Gln Asp Leu Thr Ala Ser Ser Glu
                565                 570                 575

Ser Leu Ser Asp Glu Ile Asp Phe Glu Phe Ser Thr Asp Ser Tyr Glu
            580                 585                 590

Glu Val Thr Val Gly Ser Ser Ala Ser Ser Ala Thr Ser Asn Tyr Glu
                595                 600                 605

Ser Gln Ser Ser Asn His Glu Ser Val Ser Phe Thr Ala Thr Thr Gln
    610                 615                 620

Ser Asn Glu Pro Thr Thr Ser Asn Ser Ala Asp Gly Asn Thr Val Val
625                 630                 635                 640

Val Val Val Ala Thr Asn Gln Asn Asp Ser Ala Ser Ser Gly Thr Pro
                645                 650                 655

Ser Gln Ser Ala Asn Gln Gln Thr Ser Ser Ser Ser Ser Ser Ala Thr
            660                 665                 670

Asn Ser Gln Ala Ser Gln Glu Ser Asn Pro Thr Val Ala Ser Leu Tyr
        675                 680                 685

Glu Asp Ser Ile Val Gly Ser Ala Val Thr Glu Asn Gln Ser Ser Glu
    690                 695                 700

Tyr Ser Thr Gln Ala Ser Ser Gln Glu Ser Gly Ala Lys Arg Thr Ser
705                 710                 715                 720

Asp Ser Glu Ser Ser Asn Pro Val Ser Gln Gln Ser Ser Glu Val Ser
                725                 730                 735

Ala Asp Val Thr Val Gly Ser Ile Val Pro Val Ser Thr Glu Thr Ser
            740                 745                 750

Ser Gln Ala Val Gln Thr Ser Ser Gln Ser Ser Ser Asn Val Ser Ala
        755                 760                 765

Ser Val Ser Ser Glu Val Asn Glu Pro Thr Thr Ser Thr Ser Ser Asp
    770                 775                 780

Gly Asn Thr Val Val Val Ile Val Ser Ser Asn Glu Asn Ser Glu Val
785                 790                 795                 800

Ser Ser Ser Gln Ser Ala Ser His Glu Ser Lys Pro Ser Tyr Asp Ser
                805                 810                 815

Val Ser Gln Ser Val Thr Pro Ala Trp Asn Ser Ala Ser Leu His Glu
            820                 825                 830

Gly Gln Asp Leu Thr Thr Ser Glu Ser Leu Ser Asp Glu Ile Ala
        835                 840                 845

Phe Glu Phe Ser Thr Asp Ser Tyr Glu Asp Ala Thr Val Gly Ser Ser
    850                 855                 860

Ala Ser Ala Glu Asn Ser Lys Tyr Gly Ser Gln Ser Ser Ser Asn Val
```

```
                865                 870                 875                 880
Ser Ile Ser Val Ser Thr Ser Ser Glu Gly Asn Ala Pro Thr Thr Gln
                    885                 890                 895
Ala Thr Ser Gly Thr Ser Asp Gly Asn Thr Val Val Ile Ile Val Ser
                900                 905                 910
Ser Asn Glu Asn Ser Ala Asp Ser Ser Gly Thr Pro Ser Pro Ser Pro
            915                 920                 925
Asp Gln Gln Thr Ser Ser Ser Leu Ser Ala Thr Phe Asp Ser Ile Ser
            930                 935                 940
Glu Val Gln Ser Thr Gln Ser Ser Ala Ser Ser Ser Tyr Asp Asp Thr
945                 950                 955                 960
Thr Val Gly Ser Ser Glu Ala Val Asp Gln Ser Thr His Lys Met Pro
                965                 970                 975
Thr Gln Asp Ser Thr Pro Ser Ser Ser Thr Gln Ser Thr Pro Asn Ser
            980                 985                 990
Asp Ser Glu Ser Ser Asn Pro Val Thr Gln Gln Ser Gly Gly Val Ser
            995                 1000                1005
Ile Asp Val Thr Val Gly Ser Val Asp Ser Val Ser Thr Glu Thr
    1010                1015                1020
Ser Ser Gln Ala Ser Gln Thr Ser Ser Gln Ser Thr Ser Asn Thr
    1025                1030                1035
Ala Asn Ser Ala Ala Gly Ser Ser Gly Ala Asp Ala Val Val Val
    1040                1045                1050
Phe Val Thr Ser Thr Glu Ala Thr Thr Gly Ser Phe Gly Ile Pro
    1055                1060                1065
Ser Gln Ser Thr Ser Ser Ser Ser Ser Ser Ser Glu Ile Asn
    1070                1075                1080
Asn Gln Ser Ser Glu Gln Lys Tyr Glu Ser Ser Ser Ser Glu Thr
    1085                1090                1095
Ile Thr Gln Ala Trp Asn Ser Gly Ser Leu Ala Val Glu Gln Asp
    1100                1105                1110
Asn Thr Asn Ala Ser Ala Gly Leu Ser Asp Gly Thr Val Phe Glu
    1115                1120                1125
Phe Ser Thr Asp Ser Tyr Glu Asp Gln Thr Val Gly Ser Val Val
    1130                1135                1140
Thr Gln Asp Gln Ser Val Ser Pro Thr Ser Ser Ser Ser Ser Glu
    1145                1150                1155
Tyr Asn Thr Gln Val Ser Gln Ser Ser Gln Gln Ser Glu Ser Thr
    1160                1165                1170
Arg Asn Ser Asn Ser Glu Pro Ser Asn Pro Val Thr Gln Gln Ser
    1175                1180                1185
Asp Glu Val Ser Ile Asp Val Thr Val Gly Ser Val Ser Thr Glu
    1190                1195                1200
Ser Pro Asp Pro Gln Thr Ser Ser Gln Ser Ser Ser Asn Val Ser
    1205                1210                1215
Ile Ser Val Ser Thr Ser Ser Glu Gly Asn Glu Pro Thr Thr Gln
    1220                1225                1230
Ala Thr Ser Ser Lys Ser Asp Gly Asn Thr Val Val Val Ile Val
    1235                1240                1245
Thr Thr Asn Asp Ser Ala Ser Ser Gly Thr Pro Ser Gln Thr Ser
    1250                1255                1260
Asn Gln Gln Thr Ser Ser Ser Ser Ser Ser Val Thr Asn Asn Lys
    1265                1270                1275
```

```
-continued

Ala  Ser  Gln  Glu  Thr  Ser  Pro  Thr  Val  Ala  Ser  Thr  Phe  Asp  Ser
     1280                1285                1290

Ile  Ser  Glu  Val  Gln  Ser  Thr  Gln  Ser  Ser  Ser  Ser  Ser  Ser  Tyr
     1295                1300                1305

Asp  Asp  Thr  Thr  Val  Gly  Ser  Ser  Glu  Val  Leu  Asp  Gln  Ser  Thr
     1310                1315                1320

Ser  Gln  Thr  Ser  Ser  Gln  Asn  Ser  Thr  Pro  Ser  Ser  Ser  Ala  Glu
     1325                1330                1335

Ser  Gly  Ser  Ile  Arg  Asn  Ser  Asp  Ser  Asp  Ser  Gln  Ser  Tyr  Asn
     1340                1345                1350

Pro  Val  Thr  Gln  Gln  Ser  Gly  Glu  Val  Ser  Ile  Asp  Val  Thr  Val
     1355                1360                1365

Gly  Ser  Val  Asp  Ser  Val  Ser  Thr  Glu  Thr  Ser  Ser  Gln  Ser  Thr
     1370                1375                1380

Gln  Thr  Ser  Ser  Gln  Ser  Ser  Ser  Asn  Val  Ser  Val  Ser  Val  Ser
     1385                1390                1395

Thr  Ala  Ser  Glu  Gly  Asn  Glu  Pro  Thr  Ser  Ala  Ser  Ser  Ser
     1400                1405                1410

Ser  Thr  Gln  Ser  Gly  Thr  Gln  Ser  Ala  Gln  Glu  Ser  Gly  Ser  Ile
     1415                1420                1425

His  Thr  Ser  Asn  Ser  Asp  Ser  Glu  Ser  Ser  Asn  Leu  Val  Thr  Gln
     1430                1435                1440

Gln  Ser  Ser  Ala  Ile  Asp  Ile  Asp  Val  Thr  Val  Gly  Ser  Val  Asp
     1445                1450                1455

Ser  Val  Ser  Thr  Glu  Thr  Ser  Ser  Gln  Ala  Ser  Gln  Met  Ser  Ser
     1460                1465                1470

Gln  Ser  Thr  Ser  Gly  Thr  Ser  Ser  Ser  Ala  Ala  Gly  Ser  Ser  Gly
     1475                1480                1485

Val  Asp  Ala  Val  Val  Val  Phe  Val  Thr  Ser  Thr  Glu  Ala  Thr  Thr
     1490                1495                1500

Gly  Thr  Tyr  Glu  Ser  Ser  Ser  Lys  Ala  Thr  Ser  Ser  Ser  Ser  Ser
     1505                1510                1515

Ser  Thr  Ser  Glu  Val  Ile  Thr  Gln  Val  Tyr  Gln  Ser  Gly  Ser  Ser
     1520                1525                1530

Ser  Ser  Ser  Ser  Ser  Ser  Ala  Ser  Phe  His  Phe  Thr  Asn  Gln  Thr
     1535                1540                1545

Ser  Gln  Val  Asn  Glu  Asp  Asn  Glu  Pro  Ala  Val  Ser  Thr  Glu  Thr
     1550                1555                1560

Ile  Gln  Val  Asp  Gln  Thr  Ser  Thr  Gln  Ser  Ser  Ser  Gln  Glu  Ala
     1565                1570                1575

Val  Ser  Thr  Ser  Ser  Ala  Ser  Ser  Glu  Thr  Lys  Asn  Pro  Val  Thr
     1580                1585                1590

Gln  Pro  Ala  Val  Asp  Thr  Ser  Ser  Ser  Glu  Ser  Ser  His  Ala  Phe
     1595                1600                1605

Asp  Glu  Ile  Thr  Arg  Val  Ser  Thr  Pro  Leu  Glu  Ser  Ile  Thr  Glu
     1610                1615                1620

Ala  Val  Asn  Glu  Val  Asn  Asn  Glu  Ser  Asp  Ser  Thr  Glu  Ala  Ser
     1625                1630                1635

Gln  Ile  Thr  Ser  Thr  Gly  Asn  Ala  Ser  His  Asn  His  Thr  Leu  Tyr
     1640                1645                1650

Val  Ala  Val  Lys  Val  Ser  Ser  Thr  Glu  Pro  Ile  Val  Ala  Ser  Ser
     1655                1660                1665

Val  Ala  Lys  Ser
     1670
```

```
<210> SEQ ID NO 19
<211> LENGTH: 297
<212> TYPE: PRT
<213> ORGANISM: Tetranychus urticae

<400> SEQUENCE: 19

Met Asn Leu Arg Lys Ile Leu Leu His Lys Asn Asn Leu Ile Leu Leu
1               5                   10                  15

Leu Asp Thr Arg Ser Gly Asn Ser Asn Asp Lys Lys Ser Ser Asp Ser
            20                  25                  30

Ser Ser Glu Pro Ser Ser Thr Lys Gln Thr Val Glu Pro Thr Lys Asp
        35                  40                  45

Ser Glu Ser Ser Lys Gln Ser Gln Ala Ser Glu Ser Lys Lys Asp Ser
    50                  55                  60

Ser Ser Gly Val Gln Leu Val Val Asp Thr Pro Val Ser Ser Gly Ser
65                  70                  75                  80

Ser Asp Arg Asn Gln Pro Thr Asp Thr Lys Asp Val Asp Ser Ser
                85                  90                  95

Glu Lys Thr His Asn Ser Glu Ser Lys Ile Asn Glu His Glu Thr Ser
            100                 105                 110

Thr Lys His Ser Asp Leu Tyr Ser Gln Thr Val Thr Gln Ala Trp Asn
        115                 120                 125

Ala Glu Ser Leu Ser Ala Gly Gln Asp His Thr Thr Lys Pro Asn Ala
    130                 135                 140

Ser Leu Ser Asp Glu Thr Ala Val Glu Phe Ser Ser Asp Ser Tyr Glu
145                 150                 155                 160

Asp Val Thr Val Gly Ser Ala Ala Ser Ser Glu Thr Ser Asn His Gly
                165                 170                 175

Ser Ile Ser Val Ala Ala Thr Ser Glu Ala Asn Gln Pro Thr Thr Gln
            180                 185                 190

Ser Thr Asn Ser Ser Thr Ser Asp Gly Asn Lys Val Val Ile Ile
        195                 200                 205

Thr Ser Asn Asp Asn Asp Ser Gly Ser Ser Glu Ile Pro Ser Gln Ser
    210                 215                 220

Ser Asn Gln Gln Thr Ser Ser Asn Ser Ala Ser Ala Thr Asn Asn Gln
225                 230                 235                 240

Thr Ser Gln Glu Ser Ser Ser Thr Ile Thr Ser Val His Asp Gly Val
                245                 250                 255

Asn Ala Gly Ser Asp Gln Ala Lys Asp Gln Ser Ala Leu Leu Pro Asn
            260                 265                 270

Leu Pro Leu Asn Leu Leu Lys His Leu Met Asn Leu Ala Gln Leu Gly
        275                 280                 285

Leu Gln Ile Gln Ser Leu Ile Ala Gln
    290                 295
```